United States Patent
Vidal et al.

(10) Patent No.: US 7,238,211 B2
(45) Date of Patent: Jul. 3, 2007

(54) 6-ALKOXY-2,3-DIAMINOPYRIDINE COUPLERS IN WHICH THE AMINO RADICAL IN POSITION 2 IS A DISUBSTITUTED AMINO RADICAL, AND USE OF THESE COUPLERS FOR DYEING KERATIN FIBRES

(75) Inventors: Laurent Vidal, Paris (FR); Aziz Fadli, Chelles (FR)

(73) Assignee: L'Oreal S.A., Paris (FR)

( * ) Notice: Subject to any disclaimer, the term of this patent is extended or adjusted under 35 U.S.C. 154(b) by 90 days.

(21) Appl. No.: 10/678,649

(22) Filed: Oct. 6, 2003

(65) Prior Publication Data

US 2005/0086747 A1   Apr. 28, 2005
US 2006/0090270 A9   May 4, 2006

Related U.S. Application Data

(60) Provisional application No. 60/431,698, filed on Dec. 9, 2002.

(30) Foreign Application Priority Data

Oct. 4, 2002   (FR) .................................. 02 12351

(51) Int. Cl.
   *A61K 7/13*   (2006.01)
(52) U.S. Cl. ..................... 8/405; 8/406; 8/408; 8/409; 8/410; 8/421; 8/568; 8/602; 546/249; 546/250
(58) Field of Classification Search ................... 8/405, 8/406, 408, 409, 410, 421, 568, 602; 546/249, 546/250
   See application file for complete search history.

(56) References Cited

U.S. PATENT DOCUMENTS

| | | | |
|---|---|---|---|
| 4,784,667 A | 11/1988 | Maak et al. | 8/409 |
| 5,785,717 A | 7/1998 | Maubru et al. | 8/409 |
| 6,692,540 B1* | 2/2004 | Audousset | 8/409 |
| 2001/0023514 A1* | 9/2001 | Cottard et al. | 8/406 |
| 2002/0013973 A1 | 2/2002 | Plos | 8/405 |

FOREIGN PATENT DOCUMENTS

| | | |
|---|---|---|
| DE | 32 33 540 A1 | 3/1984 |
| DE | 41 15 148 A1 | 11/1992 |
| DE | 199 36 442 A1 * | 2/2001 |
| EP | 0 728 464 B1 | 8/1996 |
| FR | 1 397 551 | 3/1965 |
| FR | 2 779 952 | 12/1999 |
| WO | WO 99/66894 * | 12/1999 |

OTHER PUBLICATIONS

English Abstract of the Patent DE 199 36 442 A1.*
Database Chemlist en ligne! 154036, XP002243965.
English language Derwent Abstract of DE 41 15 148 A1, Nov. 12, 1992.
English language Derwent Abstract of DE 199 36 442 A1, Feb. 8, 2001.
English language Derwent Abstract of FR 2 779 952, Dec. 24, 1999.

* cited by examiner

*Primary Examiner*—Eisa Elhilo
(74) *Attorney, Agent, or Firm*—Finnegan, Henderson, Farabow, Garrett & Dunner

(57) ABSTRACT

The invention relates to a dye composition that is useful for dyeing keratin fibers, containing at least one oxidation base and at least one coupler of the 6-alkoxy-2,3-diaminopyridine type in which the amino radical in position 2 is a disubstituted amino radical, to the use of this composition for dyeing keratin fibers and to the dyeing process using this composition.

The invention also relates to novel 6-alkoxy-2,3-diaminopyridine compounds that are useful as couplers.

23 Claims, No Drawings

6-ALKOXY-2,3-DIAMINOPYRIDINE COUPLERS IN WHICH THE AMINO RADICAL IN POSITION 2 IS A DISUBSTITUTED AMINO RADICAL, AND USE OF THESE COUPLERS FOR DYEING KERATIN FIBRES

The invention relates to a dye composition that is useful for dyeing keratin fibres, containing at least one oxidation base and at least one coupler of the 6-alkoxy-2,3-diaminopyridine type in which the amino radical in position 2 is a disubstituted amino radical, to the use of this composition for dyeing keratin fibres and to the dyeing process using this composition. The invention also relates to novel 6-alkoxy-2,3-diaminopyridine compounds that are useful as couplers.

It is known practice to dye keratin fibres, and in particular human hair, with dye compositions containing oxidation dye precursors, which are generally known as oxidation bases, such as ortho- or para-phenylenediamines, ortho- or para-aminophenols and heterocyclic couplers. These oxidation bases are colourless or weakly coloured compounds which, when combined with oxidizing products, can give rise to coloured compounds by a process of oxidative condensation.

It is also known that the shades obtained with these oxidation bases can be varied by combining them with couplers or coloration modifiers, these agents being chosen especially from aromatic meta-diamines, meta-aminophenols, meta-diphenols and certain heterocyclic compounds such as indole compounds.

The variety of molecules used as oxidation bases and couplers allows a wide range of colours to be obtained.

The "permanent" coloration obtained by means of these oxidation dyes must moreover satisfy a certain number of requirements. Thus, it must have no toxicological drawback, it must allow shades to be obtained in the desired strength, and it must show good fastness with respect to external agents such as light, bad weather, washing, permanent-waving, perspiration and rubbing.

The dyes must also allow white hair to be covered and, finally, they must be as unselective as possible, ie they must produce the smallest possible differences in coloration along the same keratin fibre, which is generally-differently sensitized (ie damaged) between its end and its root.

Document FR 1 397 551 describes dye compositions containing oxidation dye precursors of the trisubstituted pyridine derivative type, each of the substituents possibly being a hydroxyl, alkoxy, amino or $NR_1R_2$ radical with $R_1$ and $R_2$ representing a H, alkyl or aryl. The coloration is obtained either by oxidation in air or with an oxidizing medium containing aqueous hydrogen peroxide solution at basic pH. On account of the high oxidizability of these pyridine precursors, the dyeing results obtained on the hair have a tendency to change over time by changing colour, which turns out to be particularly unattractive.

Document DE 3 233 540 proposes hair dye compositions containing, as coupler, 6-alkoxy-3-aminopyridine derivatives substituted in position 2 with an $NH_2$ or $NHR_3$ radical with $R_3$=H, $C_1$–$C_4$ alkyl or $C_2$–$C_4$ hydroxyalkyl in combination with standard oxidation bases. These compositions give, in the presence of certain bases such as para-phenylenediamine or para-toluenediamine, dark blue shades that are unstable to light and that lack strength and uniformity between the root and the end of the hairs.

Documents DE 4 115 148, FR 2 779 952, EP 728 464 and DE 199 36 442 propose to combine particular pyridine-based couplers of this type with specific oxidation bases such as pyrazolopyrimidine, para-aminophenol, pyrimidine or 4,5- or 3,4-diaminopyrazole bases.

However, none of these compositions make it possible to obtain strong colorations in varied shades that are uniform from the root to the end of the hairs, that show little selectivity and particularly good resistance, and that have good chromaticity.

This aim is achieved with the present invention, one subject of which is a dye composition comprising, in a medium that is suitable for dyeing,
at least one oxidation base, and
at least one 6-alkoxy-2,3-diaminopyridine coupler of formula (I) or a corresponding addition salt thereof:

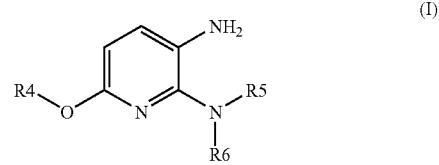

in which:
$R_4$ represents a linear or branched $C_1$–$C_4$ alkyl radical optionally substituted with one or more hydroxyl, $C_1$–$C_2$ alkoxy or $NR_7R_8$ radicals in which $R_7$ and $R_8$ are chosen from a hydrogen atom, a $C_1$–$C_4$ alkyl, a $C_2$–$C_6$ (poly)hydroxyalkyl, a $C_2$–$C_6$ (poly)aminoalkyl or a $C_2$–$C_6$ aminohydroxyalkyl;

$R_5$ represents a linear or branched $C_1$–$C_6$ alkyl radical optionally substituted with one or more radicals chosen from $C_1$–$C_2$ alkoxy, hydroxyl, carboxyl, sulphonic (—$SO_3H$) or $NR_9R_{10}$ radicals; a 2-acylaminoethyl radical; a 2-(2-hydroxyethyloxy)ethyl radical;

$R_6$ represents a linear or branched $C_1$–$C_6$ alkyl radical optionally substituted with one or more radicals chosen from $C_1$–$C_2$ alkoxy, hydroxyl, carboxyl, sulphonic, $NR'_9R'_{10}$ or acylamino radicals (RCONH— with R being a $C_1$–$C_4$ alkyl); a 2-(2-hydroxyethyloxy)ethyl radical;

$R_9$, $R_{10}$, $R_9'$ and $R_{10}'$ denote, independently of each other, a hydrogen atom; a $C_1$–$C_4$ alkyl radical optionally substituted with one or more hydroxyl, amino, monoalkylamino, dialkylamino, alkoxy or acylamino radicals.

In the context of the present invention, the term "alkyl" means linear or branched radicals, for example methyl, ethyl, n-propyl, isopropyl, butyl, etc., cycloalkyl radicals such as cyclobutyl, cyclopentyl, cyclohexyl, diazepane radicals, etc. An alkoxy radical is a radical alk-O, the alkyl radical having the definition given above.

By way of example, $R_5$ and $R_6$ independently represent a methyl, ethyl, propyl, hydroxyethyl, for example 2-hydroxyethyl, aminoethyl, for example 2-aminoethyl, carboxyethyl, for example 2-carboxyethyl, acylaminoethyl, hydroxypropyl, for example 2-hydroxypropyl or 3-hydroxypropyl, aminopropyl, for example 3-aminopropyl, N,N-dimethylaminoethyl, for example 2-N,N-dimethylaminoethyl, N-methylaminoethyl, for example 2-N-methylaminoethyl, (2-hydroxyethylamino)ethyl or (2-hydroxyethyloxy)ethyl radical.

Preferably, $R_5$ represents a $C_1$–$C_4$ alkyl radical optionally substituted with one or more radicals chosen from hydroxyl, $C_1$–$C_2$ alkoxy, amino, $C_1$–$C_2$ (di)alkylamino, carboxyl, $C_1$–$C_2$ (di)hydroxyalkylamino or sulphonic radicals; a 2-acylaminoethyl radical; a 2-(2-hydroxyethyloxy)ethyl radical. In particular, $R_5$ represents an alkyl radical or an alkyl radical substituted with one or more radicals chosen from a hydroxyl, $C_1$–$C_2$ alkoxy, amino, $C_1$–$C_2$ (di)alkylamino, carboxyl or $C_1$–$C_2$ (di)hydroxyalkylamino; a 2-acylaminoethyl radical; a 2-(2-hydroxyethyloxy)ethyl radical. According to one particularly preferred embodiment, $R_5$ represents a methyl, ethyl, propyl, 2-hydroxyethyl, 2-aminoethyl, 2-carboxyethyl, 2-acylaminoethyl, 2-hydroxypropyl, 3-hydroxypropyl, 3-aminopropyl, 2-N,N-dimethylaminoethyl, 2-N-methylaminoethyl, 2-(2-hydroxyethylamino)ethyl or 2-(2-hydroxyethyloxy)ethyl radical.

According to one particular embodiment, $R_6$ represents a substituted alkyl radical.

By way of example, $R_6$ represents a hydroxyethyl, aminoethyl, carboxyethyl, acylaminoethyl, hydroxypropyl, aminopropyl, N,N-dimethylaminoethyl, N-methylaminoethyl, (2-hydroxyethylamino)ethyl or (2-hydroxyethyloxy)ethyl radical.

Preferably, $R_6$ represents a $C_1$–$C_4$ alkyl radical substituted with one or more radicals chosen from hydroxyl, $C_1$–$C_2$ alkoxy, amino, $C_1$–$C_2$ (di)alkylamino, carboxyl, acylamino, $C_1$–$C_2$ (di)hydroxyalkylamino or sulphonic radicals; a 2-(2-hydroxyethyloxy)ethyl radical, in particular $R_6$ is a $C_1$–$C_4$ alkyl radical substituted with one or more radicals chosen from a hydroxyl, $C_1$–$C_2$ alkoxy, amino, $C_1$–$C_2$ (di)alkylamino, carboxyl, acylamino or (di)hydroxyalkylamino; a 2-(2-hydroxyethyloxy)ethyl radical.

According to one particularly preferred embodiment, $R_6$ represents a 2-hydroxyethyl, 2-aminoethyl, 2-carboxyethyl, 2-acylaminoethyl, 2-hydroxypropyl, 3-hydroxypropyl, 3-aminopropyl, 2-N,N-dimethylaminoethyl, 2-N-methylaminoethyl, 2-(2-hydroxyethylamino)ethyl or 2-(2-hydroxyethyloxy)ethyl radical.

In formula (I), $R_4$ preferably represents a $C_1$–$C_4$ alkyl radical optionally substituted with one or more hydroxyl or $C_1$–$C_2$ alkoxy radicals. Preferably, $R_4$ preferably represents a $C_1$–$C_4$ alkyl radical.

According to one particular embodiment, $R_5$ is an alkyl radical and $R_6$ is an alkyl radical substituted with one or more hydroxyl. According to another embodiment, $R_5$ and $R_6$ represent an alkyl radical substituted with one or more hydroxyl.

The compounds of formula (I) are for example the compounds

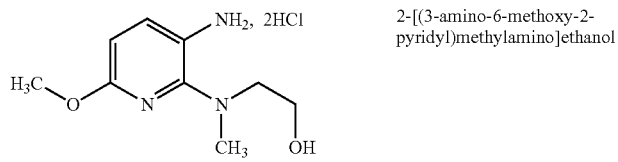

2-[(3-amino-6-methoxy-2-pyridyl)methylamino]ethanol

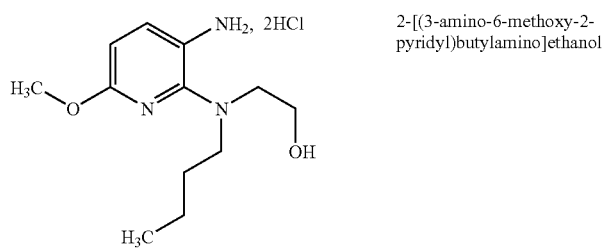

2-[(3-amino-6-methoxy-2-pyridyl)butylamino]ethanol

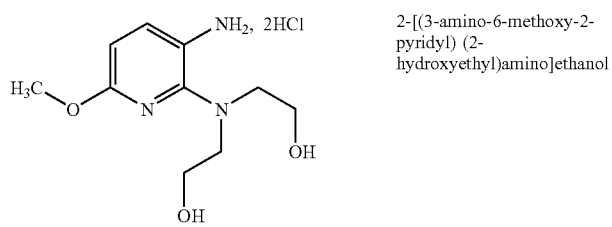

2-[(3-amino-6-methoxy-2-pyridyl) (2-hydroxyethyl)amino]ethanol

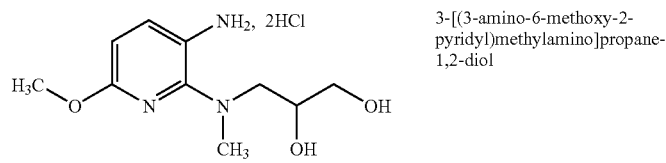

3-[(3-amino-6-methoxy-2-pyridyl)methylamino]propane-1,2-diol

-continued
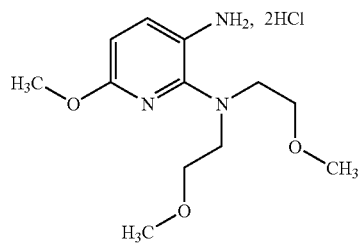
6-methoxy-N2,N2-bis(2-methoxyethyl)pyridine-2,3-diamine
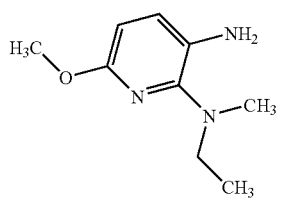
6-methoxy-N2-ethyl-N2-methylpyridine-2,3-diamine
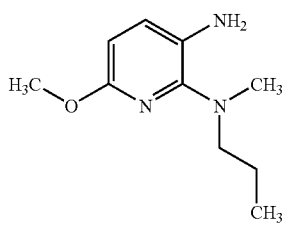
6-methoxy-N2-methyl-N2-propylpyridine-2,3-diamine
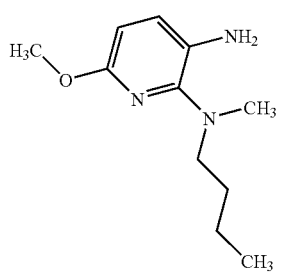
6-methoxy-N2-butyl-N2-methylpyridine-2,3-diamine
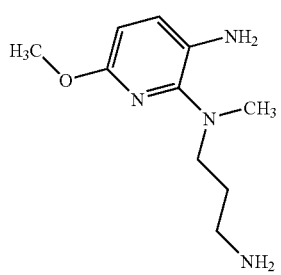
6-methoxy-N2-(3-aminopropyl)-N2-methylpyridine-2,3-diamine
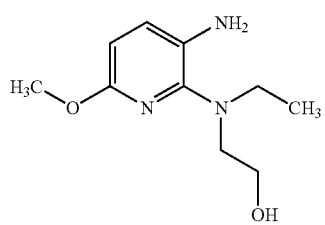
2-[(3-amino-6-methoxy-2-pyridyl)ethylamino]ethanol -continued
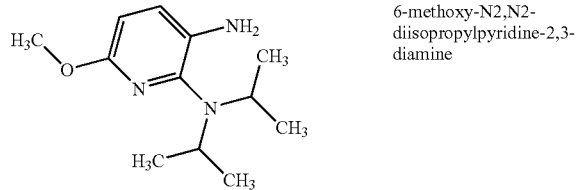
6-methoxy-N2,N2-diisopropylpyridine-2,3-diamine
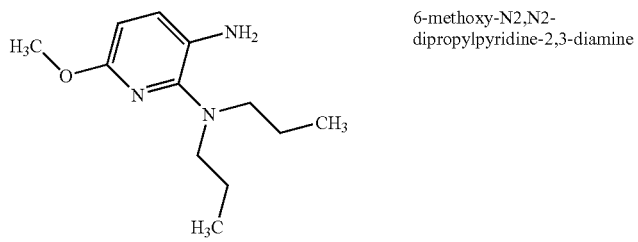
6-methoxy-N2,N2-dipropylpyridine-2,3-diamine
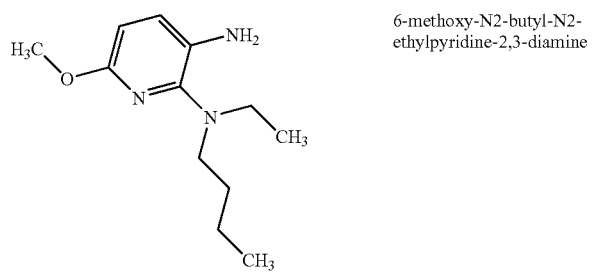
6-methoxy-N2-butyl-N2-ethylpyridine-2,3-diamine
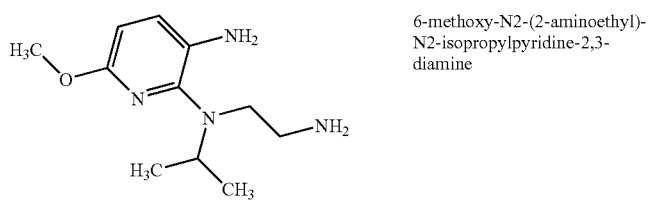
6-methoxy-N2-(2-aminoethyl)-N2-isopropylpyridine-2,3-diamine
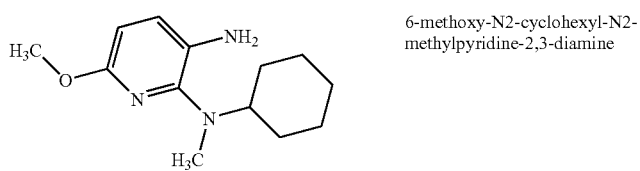
6-methoxy-N2-cyclohexyl-N2-methylpyridine-2,3-diamine
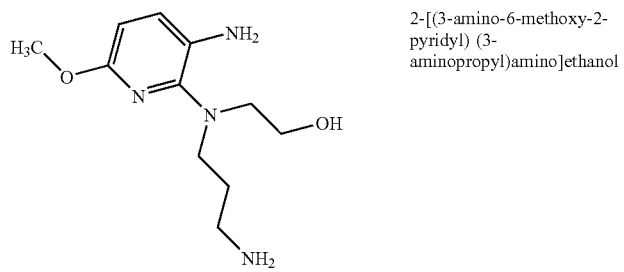
2-[(3-amino-6-methoxy-2-pyridyl) (3-aminopropyl)amino]ethanol
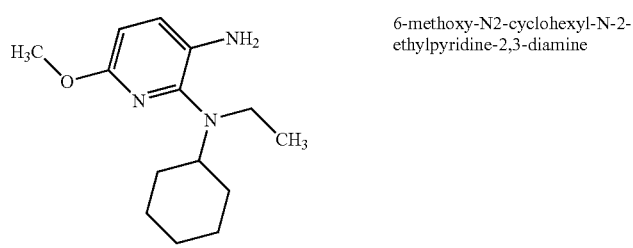
6-methoxy-N2-cyclohexyl-N-2-ethylpyridine-2,3-diamine -continued

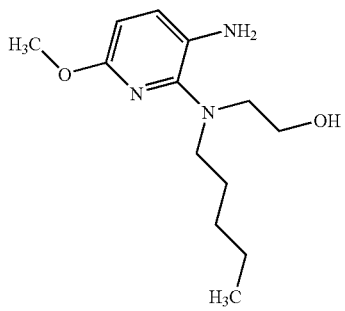

2-[(3-amino-6-methoxy-2-pyridyl)pentylamino]ethanol

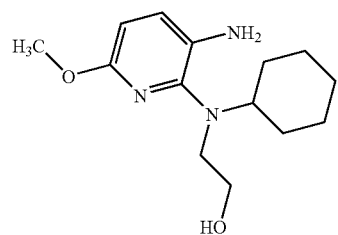

2-[(3-amino-6-methoxy-2-pyridyl)cyclohexylamino]-ethanol

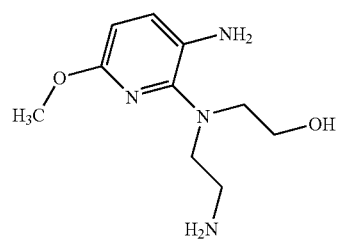

2-[(3-amino-6-methoxy-2-pyridyl) (2-aminoethyl)amino]ethanol

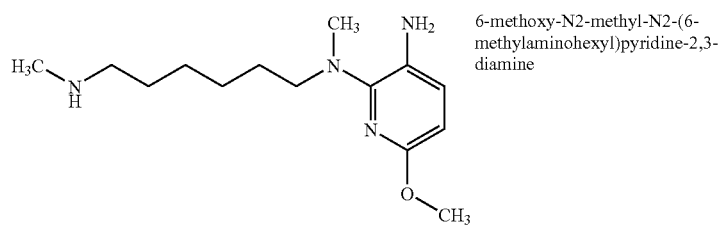

6-methoxy-N2-methyl-N2-(6-methylaminohexyl)pyridine-2,3-diamine and the addition salts thereof.

The oxidation dye composition of the present invention comprises one or more oxidation bases conventionally used in oxidation dyeing. By way of example, these additional oxidation bases are chosen from para-phenylenediamines, bis(phenyl)alkylenediamines, para-aminophenols, bis-para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis-(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof with an acid.

Among the para-aminophenols that may be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof with an acid.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Other pyridine oxidation bases that are useful in the present invention are the 3-aminopyrazolo[1,5-a]pyridine oxidation bases or addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamino, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazol[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof with an acid or with a base.

Among the pyrimidine derivatives that may be mentioned are the compounds described, for example, in patents DE 2 359 399; JP 88-169 571; JP 05-63124; EP 0 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, pyrazolopyrimidine derivatives such as those mentioned in patent application FR-A-2 750 048, and among which mention may be made of pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,-N7,N7-tetramethylpyrazolo[1,5-a]pyrimidine-3,7-diamine and 3-amino-5-methyl-7-imidazolylpropylaminopyrazolo[1,5-a]pyrimidine, and the addition salts thereof with an acid, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

The oxidation base(s) present in the composition of the invention is (are) each generally present in an amount of between 0.001% and 10% by weight approximately, and preferably between 0.005% and 6%, relative to the total weight of the dye composition.

The composition according to the invention may contain one or more additional conventional couplers other than the coupler of formula (I). Among these additional couplers that may especially be mentioned are meta-phenylenediamines, meta-aminophenols, meta-diphenols, naphthalene-based couplers and heterocyclic couplers other than the couplers described above, and the addition salts thereof.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the addition salts thereof with an acid.

In the composition of the present invention, the coupler(s) is (are) each generally present in an amount of between 0.001% and 10% by weight approximately, and preferably between 0.005% and 6%, relative to the total weight of the dye composition.

In general, the addition salts of the oxidation bases and of the couplers that may be used in the context of the invention are chosen especially from the addition salts with an acid, such as the hydrochlorides, hydrobromides, sulphates, citrates, succinates, tartrates, lactates, tosylates, benzenesulphonates, phosphates and acetates, and the addition salts with a base, such as sodium hydroxide, potassium hydroxide, aqueous ammonia, amines or alkanolamines.

The dye composition in accordance with the invention may also contain one or more direct dyes that may be chosen especially from nitrobenzene dyes, azo direct dyes and methine direct dyes. These direct dyes may be of nonionic, anionic or cationic nature.

The dye composition of the present invention is particularly useful for dyeing keratin fibres, in particular human keratin fibres. In this case, the medium is a cosmetic medium that is suitable for dyeing these fibres.

This medium that is suitable for dyeing, also known as a dye support, generally consists of water or of a mixture of water and of at least one organic solvent to dissolve the compounds that would not be sufficiently soluble in the water. Examples of organic solvents that may be mentioned include $C_1$–$C_4$ lower alkanols, such as ethanol and isopropanol; polyols and polyol ethers, for instance 2-butoxyethanol, propylene glycol, propylene glycol monomethyl ether, diethylene glycol monoethyl ether and monomethyl ether, and also aromatic alcohols, for instance benzyl alcohol or phenoxyethanol, and mixtures thereof.

The solvents are preferably present in proportions preferably of between 1% and 40% by weight approximately and even more preferably between 5% and 30% by weight approximately relative to the total weight of the dye composition.

The dye composition in accordance with the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrating agents, sequestering agents, fragrances, buffers, dispersants, conditioners, for instance volatile or non-volatile, modified or unmodified silicones, film-forming agents, ceramides, preserving agents and opacifiers.

The above adjuvants are generally present in an amount for each of between 0.01% and 20% by weight relative to the weight of the composition.

Needless to say, a person skilled in the art will take care to select this or these additional optional compound(s) such that the advantageous properties intrinsically associated with the oxidation dye composition in accordance with the invention are not, or are not substantially, adversely affected by the envisaged addition(s).

The pH of the dye composition in accordance with the invention is generally between 3 and 12 approximately and preferably between 5 and 11 approximately. It may be adjusted to the desired value by means of acidifying or basifying agents usually used for dyeing keratin fibres, or alternatively using standard buffer systems.

Among the acidifying agents that may be mentioned, for example, are mineral or organic acids, for instance hydrochloric acid, orthophosphoric acid, sulphuric acid, carboxylic acids, for instance acetic acid, tartaric acid, citric acid or lactic acid, and sulphonic acids.

Among the basifying agents that may be mentioned, for example, are aqueous ammonia, alkaline carbonates, alkanolamines such as monoethanolamine, diethanolamine and triethanolamine and derivatives thereof, sodium hydroxide, potassium hydroxide and the compounds of formula (II) below:

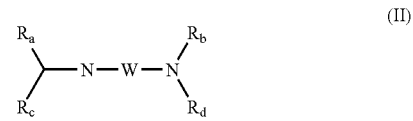

(II)

in which W is a propylene residue optionally substituted with a hydroxyl group or a $C_1$–$C_4$ alkyl radical; $R_a$, $R_b$, $R_c$ and $R_d$, which may be identical or different, represent a hydrogen atom or a $C_1$–$C_4$ alkyl or $C_1$–$C_4$ hydroxyalkyl radical.

The dye composition according to the invention may be in various forms, such as in the form of liquids, creams or gels, or in any other form that is suitable for dyeing keratin fibres, and especially human hair.

The process of the present invention is a process in which the composition according to the present invention as defined above is applied to the fibres, in the presence of an oxidizing agent, for a time that is sufficient to develop the desired coloration. The colour may revealed at acidic, neutral or alkaline pH and the oxidizing agent may be added to the composition of the invention just at the time of use, or it may be introduced using an oxidizing composition containing it, applied simultaneously with or sequentially to the composition of the invention.

According to one particular embodiment, the composition according to the present invention is mixed, preferably at the time of use, with a composition containing, in a medium that is suitable for dyeing, at least one oxidizing agent, this oxidizing agent being present in an amount that is sufficient to develop a coloration. The mixture obtained is then applied to the keratin fibres. After a leave-in time of 3 to 50 minutes approximately and preferably 5 to 30 minutes approximately, the keratin fibres are rinsed, washed with shampoo, rinsed again and then dried.

The oxidizing agents conventionally used for the oxidation dyeing of keratin fibres are, for example, hydrogen peroxide, urea peroxide, alkali metal bromates, persalts such as perborates and persulphates, peracids, and oxidase enzymes, among which mention may be made of peroxidases, 2-electron oxidoreductases such as uricases, and 4-electron oxygenases, for instance laccases. Hydrogen peroxide is particularly preferred.

The oxidizing composition may also contain various adjuvants conventionally used in hair dye compositions and as defined above.

The pH of the oxidizing composition containing the oxidizing agent is such that, after mixing with the dye composition, the pH of the resulting composition applied to the keratin fibres preferably ranges between 3 and 12 approximately and even more preferably between 5 and 11. It may be adjusted to the desired value by means of acidifying or basifying agents usually used in the dyeing of keratin fibres and as defined above.

The ready-to-use composition that is finally applied to the keratin fibres may be in various forms, such as in the form of liquids, creams or gels, or in any other form that is suitable for dyeing keratin fibres, and especially human hair.

The composition of the invention may be in the form of a kit. Such a kit comprises a composition as defined above on the one hand, and an oxidizing composition on the other hand.

A subject of the invention is also a multi-compartment device, in which a first compartment contains the dye composition of the present invention defined above and a second compartment contains an oxidizing agent. This device may be equipped with a means for applying the desired mixture to the hair, such as the devices described in patent FR 2 586 913 in the name of the Applicant.

Using this device, it is possible to dye keratin fibres using a process that involves mixing a dye composition of the invention with an oxidizing agent, and applying the mixture obtained to the keratin fibres for a time that is sufficient to develop the desired coloration.

Finally, a subject of the present invention is the 6-alkoxy-2,3-diaminopyridine compounds of formula (I), and the corresponding addition salts thereof as defined above, with the exception of 2-(N-methyl-N-(β-hydroxyethyl)amino)-3-amino-6-methoxypyridine.

These compounds may be synthesized according to the following synthetic scheme:

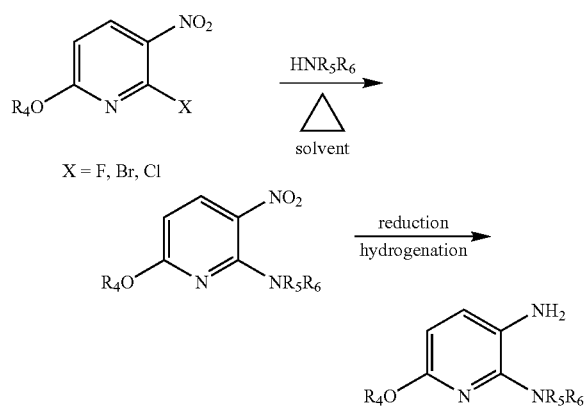

The first step consists in reacting a 6-alkoxy-3-nitro-2-halopyridine derivative with an amine of the type $HNR_5R_6$ in which $R_5$ and $R_6$ have the same meanings given above, in a polar solvent with a boiling point of between 70° C. and 180° C. The reaction temperature varies, according to the pyridine derivatives and the nucleophilic amine, from 75° C. to 140° C. The solvent that will be chosen is preferably alcohols such as ethanol, isopropanol, butanol or pentanol, and also acetic acid, formic acid, dioxane or DMF.

The second step is a reduction reaction performed either by hydrogenation under heterogeneous catalysis, or by hydrogen transfer, or alternatively with metal hydrides or with a formic acid/acetic acid couple in the presence of palladium.

For example, the method, widely illustrated in the literature, of hydrogenation catalyzed with palladium(0), Pd (II) or Raney nickel or $PtO_2$, is used.

The hydrogen-transfer reduction by reacting cyclohexene in the presence of palladium is also found to be very effective.

The examples that follow serve to illustrate the invention without, however, being limiting in nature.

EXAMPLES OF SYNTHESIS

Example 1

2-[(3-Amino-6-methoxy-2-pyridyl)methylamino]ethanol

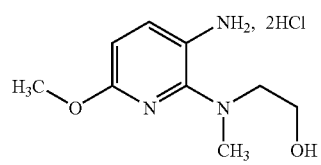

A) Synthesis of 2-[(6-methoxy-3-nitro-2-pyridyl)methylamino]ethanol 1.9 g (0.01 mol) of the product 2-chloro-3-nitro-6-methoxypyridine, 30 ml of dioxane, 5 ml of water and 1.6 ml (0.02 mol) of 2-methylaminoethanol are placed in a fully equipped round-bottomed flask. The mixture is refluxed for 2 hours with stirring and is then poured onto an ice/water mixture with stirring. The precipitate formed is filtered off by suction and dried under vacuum to constant weight. 1.6 g of yellow powder are obtained, ie a yield of 70%.

B) Synthesis of 2-[(3-amino-6-methoxy-2-pyridyl)methylamino]ethanol 1.6 g (0.007 mol) of the product 2-[(6-methoxy-3-nitro-2-pyridyl)methylamino]ethanol synthesized according to procedure (A) above, 15 ml of ethanol, 5 ml of cyclohexene and 0.5 g of palladium-on-charcoal are placed in a fully equipped round-bottomed flask. The mixture is refluxed for 2 hours with stirring, the catalyst is then removed by filtration and the filtrate is then acidified with hydrochloric acid. After dilution with diisopropyl ether, the precipitate formed is filtered off by suction and dried under vacuum to constant weight. 2.0 g of powder are obtained, ie a yield of 100%.

Analysis by mass spectrometry and magnetic resonance spectroscopy is in accordance with the expected structure.

Weight analysis

| | | | | | |
|---|---|---|---|---|---|
| Found: | C 39.93 | H 6.33 | N 15.52 | O 13.00 | Cl 24.93 |
| Calculated: | C 40.01 | H 6.34 | N 15.55 | O 11.84 | Cl 26.25 |

Example 2

2-[(3-Amino-6-methoxy-2-pyridyl)butylamino]ethanol

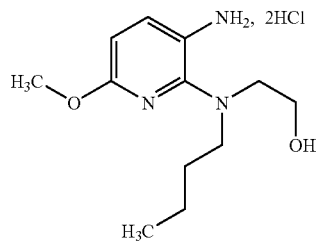

A) Synthesis of 2-[butyl-(6-methoxy-3-nitro-2-pyridyl)amino]ethanol 1.9 g (0.01 mol) of the product 2-chloro-3-nitro-6-methoxypyridine, 30 ml of dioxane, 5 ml of water and 2.62 ml (0.02 mol) of 2-butylaminoethanol are placed in a fully equipped round-bottomed flask. The mixture is refluxed for 2 hours with stirring and is then poured onto an ice/water mixture with stirring. The precipitate formed is filtered off by suction and dried under vacuum to constant weight. 1.9 g of yellow powder are obtained, ie a yield of 70%.

B) Synthesis of 2-[(3-amino-6-methoxy-2-pyridyl)butylamino]ethanol 1.9 g (0.007 mol) of the product 2-[butyl-(6-methoxy-3-nitro-2-pyridyl)amino]ethanol synthesized according to procedure (A) above, 15 ml of ethanol, 5 ml of cyclohexene and 0.5 g of palladium-on-charcoal are placed in a fully equipped round-bottomed flask. The mixture is refluxed for 2 hours with stirring, the catalyst is then removed by filtration and the filtrate is then acidified with hydrochloric acid. After dilution with diisopropyl ether, the precipitate formed is filtered off by suction and dried under vacuum to constant weight. 1.63 g of powder are obtained, ie a yield of 84.5%.

Analysis by mass spectrometry and magnetic resonance spectroscopy is in accordance with the expected structure.

Example 3

2-[(3-Amino-6-methoxy-2-pyridyl)(2-hydroxyethyl)amino]ethanol

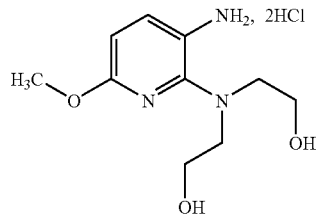

A) Synthesis of 2-[(2-hydroxyethyl)(6-methoxy-3-nitro-2-pyridyl)amino]ethanol 1.9 g (0.01 mol) of the product 2-chloro-3-nitro-6-methoxypyridine, 30 ml of dioxane, 5 ml of water and 2.1 ml (0.02 mol) of diethanolamine are placed in a fully equipped round-bottomed flask. The mixture is refluxed for 2 hours with stirring and is then poured onto an ice/water mixture with stirring. The precipitate formed is filtered off by suction and dried. 1.9 g of yellow powder are obtained, ie a yield of 74%.

B) Synthesis of 2-[(3-amino-6-methoxy-2-pyridyl)(2-hydroxyethyl)amino]ethanol 2 g (0.0078 mol) of the product 2-[(2-hydroxyethyl)(6-methoxy-3-nitro-2-pyridyl)amino]ethanol synthesized according to procedure (A) above, 15 ml of ethanol, 5 ml of cyclohexene and 0.5 g of palladium-on-charcoal are placed in a fully equipped round-bottomed flask. The mixture is refluxed for 2 hours with stirring, the catalyst is then removed by filtration and the filtrate is then acidified with hydrochloric acid. After dilution with diisopropyl ether, the precipitate formed is filtered off by suction and dried under vacuum to constant weight. 2.21 g of powder are obtained, ie a yield of 100%.

Analysis by mass spectrometry and magnetic resonance spectroscopy is in accordance with the expected structure.

Weight analysis Found: C, 39.7; H, 6.46; N, 13.73; O, 16.26; Cl, 22.94. Calculated: C, 40.01; H, 6.38; N, 14; O, 15.99; Cl, 23.62.

Example 4

3-[(3-Amino-6-methoxy-2-pyridyl)methylamino]propane-1,2-diol

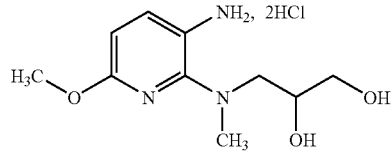

A) Synthesis of 3-[(6-methoxy-3-nitro-2-pyridyl)methylamino]propane-1,2-diol 4 g (0.0219 mol) of the product 2-chloro-3-nitro-6-methoxypyridine, 50 ml of ethanol and 4.15 ml (0.0438 mol) of 3-methylamino-1,2-dihydroxypropane are placed in a fully equipped round-bottomed flask. The mixture is refluxed for 2 hours with stirring and is then poured onto an ice/water mixture with stirring. The precipitate formed is filtered off by suction and dried under vacuum to constant weight. 4.74 g of yellow powder are obtained, ie a yield of 87.1%.

B) Synthesis of 3-[(3-amino-6-methoxy-2-pyridyl)methylamino]propane-1,2-diol 4.65 g (0.018 mol) of the product 3-[(6-methoxy-3-nitro-2-pyridyl)methylamino]propane-1,2-diol synthesized according to procedure (A) above, 50 ml of ethanol, 10 ml of cyclohexene and 2.1 g of palladium-on-charcoal are placed in a fully equipped round-bottomed flask. The mixture is refluxed for 2 hours with stirring, the catalyst is then removed by filtration and the filtrate is then acidified with hydrochloric acid. After dilution with diisopropyl ether, the precipitate formed is filtered off by suction and dried under vacuum to constant weight. 4.33 g of powder are obtained, ie a yield of 91%.

Analysis by mass spectrometry and magnetic resonance spectroscopy is in accordance with the expected structure.

Weight analysis: Found: C, 39.70; H, 6.71; N, 10.87; O, 19.65. Calculated: C, 40.01; H, 6.38; N, 14; O, 15.99; Cl, 23.62.

Example 5

6-Methoxy-N2,N2-bis(2-methoxyethyl)pyridine-2,3-diamine

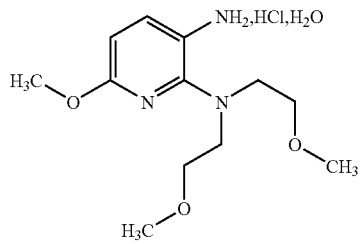

A) Synthesis of bis(2-methoxyethyl)(6-methoxy-3-nitro-2-pyridyl)amine 4 g (0.0212 mol) of the product 2-chloro-3-nitro-6-methoxypyridine, 50 ml of ethanol and 6.32 ml (0.0424 mol) of bis(2-methoxyethyl)amine are placed in a fully equipped round-bottomed flask. The mixture is refluxed for 2 hours with stirring and is then poured onto an ice/water mixture with stirring. The precipitate formed is filtered off by suction and dried under vacuum to constant weight. 5.47 g of yellow powder are obtained, ie a yield of 90.6%.

B) Synthesis of 6-methoxy-N2,N2-bis(2-methoxyethyl)-pyridine-2,3-diamine 5.3 g (0.0186 mol) of the product bis(2-methoxyethyl)(6-methoxy-3-nitro-2-pyridyl)amine synthesized according to procedure (A) above, 40 ml of ethanol, 15 ml of cyclohexene and 2.3 g of palladium-on-charcoal are placed in a fully equipped round-bottomed flask. The mixture is refluxed for 2 hours with stirring, the catalyst is then removed by filtration and the filtrate is then acidified with hydrochloric acid. After dilution with diisopropyl ether, the precipitate formed is filtered off by suction and dried under vacuum to constant weight. 4.96 g of powder are obtained, ie a yield of 91.3%.

Analysis by mass spectrometry and magnetic resonance spectroscopy is in accordance with the expected structure.

Weight analysis:

| | | | | | |
|---|---|---|---|---|---|
| Found: | C 47.6 | H 7.36 | N 13.7 | O 17.85 | Cl 13.45 |
| Calculated: | C 46.53 | H 7.81 | N 13.56 | O 20.66 | Cl 11.44 |

Examples 6 to 21

The following 6-alkoxy-2,3-diaminopyridine compounds were obtained according to the process described for Example 1B, starting with the nitro compounds indicated in the table below.

| | Nitro compounds | 6-Alkoxy-2,3-diaminopyridine compounds according to the invention | Found mass | Theoretical mass |
|---|---|---|---|---|
| Ex. 6 | [structure: 6-methoxy-3-nitro-2-(N-methyl-N-ethyl)aminopyridine] | [structure: 6-methoxy-2,3-diaminopyridine derivative, NH₂, 2HCl] | 217 | 217.70 |
| Ex. 7 | [structure: 2-(N-methyl-N-ethyl)amino-3-nitro-6-methoxypyridine] | [structure: diaminopyridine, NH₂, 2HCl] | 231 | 231.72 |

-continued

| Nitro compounds | 6-Alkoxy-2,3-diaminopyridine compounds according to the invention | Found mass | Theoretical mass |
|---|---|---|---|
| Ex. 8 | | 245 | 245.75 |
| Ex. 9 | | 246 | 246.74 |
| Ex. 10 | | 247 | 247.72 |
| Ex. 11 | | 259 | 259.78 |
| Ex. 12 | | 259 | 259.78 |

-continued
| | Nitro compounds | 6-Alkoxy-2,3-diaminopyridine compounds according to the invention | Found mass | Theoretical mass |
|---|---|---|---|---|
| Ex. 13 | 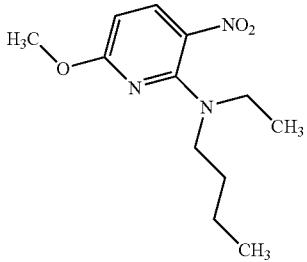 | | 259 | 259.78 |
| Ex. 14 | 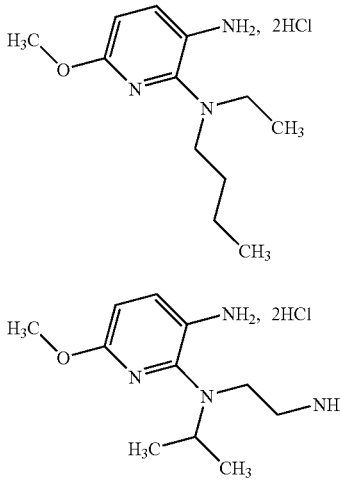 | | 260 | 260.76 |
| Ex. 15 | 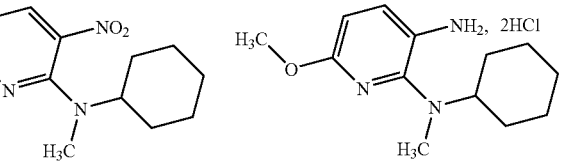 | | 271 | 271.79 |
| Ex. 16 | 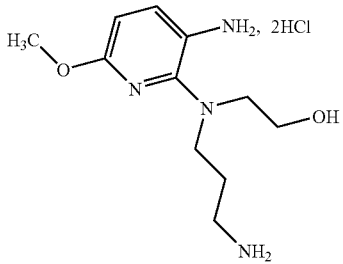 | | 276 | 276.76 |
| Ex. 17 | 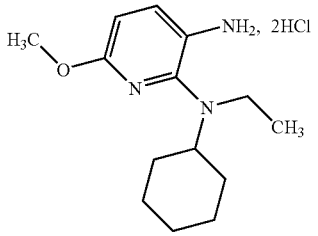 | | 285 | 285.81 |
| Ex. 18 | 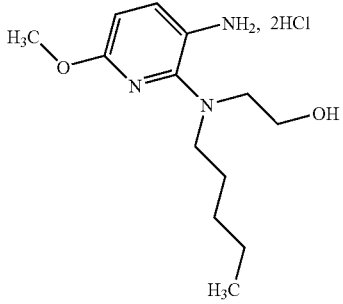 | | 289 | 289.80 |

| Nitro compounds | 6-Alkoxy-2,3-diaminopyridine compounds according to the invention | Found mass | Theoretical mass |
|---|---|---|---|
| Ex. 19 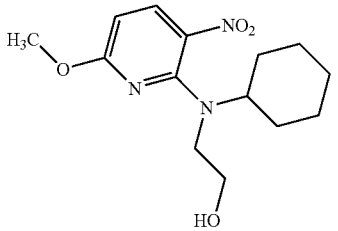 | 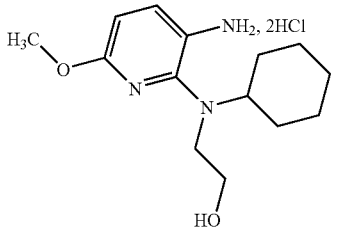 | 301 | 301.81 |
| Ex. 20 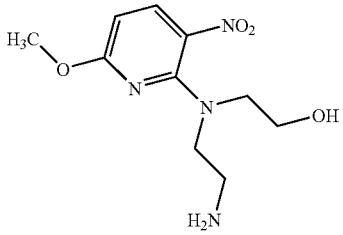 | 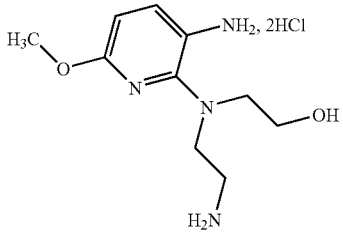 | 262 | 262.74 |
| Ex. 21 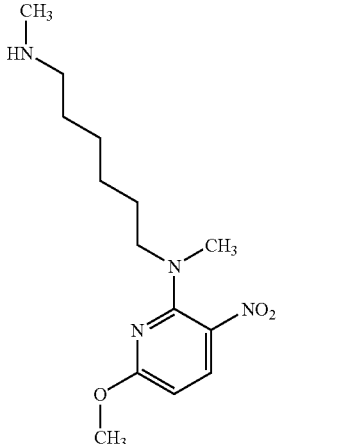 | 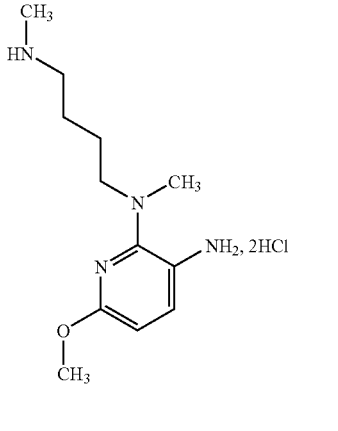 | 302 | 302.85 |

EXAMPLES OF DYEING

Example 1

Of Dyeing in Acidic Medium

The dye composition below was prepared:

| | |
|---|---|
| para-Phenylenediamine | $5 \times 10^{-3}$ mol |
| 2-[(3-Amino-6-methoxy-2-pyridyl)butylamino]ethanol | $5 \times 10^{-3}$ mol |
| Dye support | (*) |
| Demineralized water qs | 100 g |

(*) Dye support

| | |
|---|---|
| 96° ethanol | 20 g |
| Sodium metabisulphite as an aqueous 35% solution | 0.23 g AM |
| Pentasodium salt of diethylenetriaminepentaacetic acid as an aqueous 40% solution | 0.48 g AM |
| $C_8$–$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

The composition is mixed at the time of use with an equal weight of 20-volumes aqueous hydrogen peroxide solution (6% by weight). The pH of the final composition is equal to 7. The mixture obtained is applied to locks of grey hair containing 90% white hairs. After a leave-in time of 30 minutes, the locks are washed with a standard shampoo, rinsed and then dried. Each lock is evaluated before and after dyeing in the L*a*b* system, using a Minolta® CM 2002 spectrocolorimeter (luminant D65).

In the L*a*b* space, the lightness is indicated by the value L* on a scale from 0 to 100, while the chromatic coordinates are expressed by a* and b*, which indicate two colour axes, a* the red-green axis, and b* the yellow-blue axis. According to this system, the higher the value of L*, the lighter and weaker the colour. Conversely, the lower the value of L*, the darker or stronger the colour.

The dyeing results below were obtained:

| Natural hair | | | Permanent-waved hair | | |
|---|---|---|---|---|---|
| L* | a* | b* | L* | a* | b* |
| 16.44 | 2.03 | −5.09 | 9.51 | 1.97 | −2.97 |

Examples 2 to 7

Of Dyeing in Alkaline Medium

The dye compositions were prepared in the following proportions:

| Example | 2 | 3 | 4 | 5 | 6 | 7 |
|---|---|---|---|---|---|---|
| 6-Methoxy-N2-ethyl-N2-methylpyridine-2,3-diamine | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — | — |
| Benzene-1,4-diamine hydrochloride | — | $10^{-3}$ mol | — | — | — | — |
| 2-[(4-Aminophenyl) (2-hydroxyethyl)amino] ethanol sulphate | — | — | $10^{-3}$ mol | — | — | — |
| 2-Ethyl-5-methyl-2H-pyrazole-3,4-diamine hydrochloride | — | — | — | $10^{-3}$ mol | — | — |
| 5-Methylpyrazolo[1,5-a]pyrimidine-3,7-diamine hydrochloride | — | — | — | — | $10^{-3}$ mol | — |
| 2-(4,5-Diaminopyrazol-1-yl) ethanol hydrochloride | — | — | — | — | — | $10^{-3}$ mol |
| Dye support (1) | (*) | (*) | (*) | (*) | (*) | (*) |
| Demineralized water qs | 100 g | 100 g | 100 g | 100 g | 100 g | 100 g |

(*) Dye support (1) pH 9.5

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| $C_8$–$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 3.2 g |

Each composition is mixed at the time of use with an equal weight of 20-volumes aqueous hydrogen peroxide solution (6% by weight). A final pH of 9.5 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 2 | 3 | 4 | 5 | 6 | 7 |
|---|---|---|---|---|---|---|
| Shade observed | red-brown | strong grey | strong blue-grey | grey | strong violet | strong violet |

Examples 8 to 11

Of Dyeing in Alkaline Medium

The dye compositions were prepared in the following proportions:

| Example | 8 | 9 | 10 | 11 |
|---|---|---|---|---|
| 6-Methoxy-N2-ethyl-N2-propylpyridine-2,3-diamine | $10^{-3}$ mol | $10^{-3}$ mol | $10^{-3}$ mol | $10^{-3}$ mol |
| Benzene-1,4-diamine hydrochloride | $10^{-3}$ mol | — | — | — |
| 2-[(4-Aminophenyl) (2-hydroxyethyl) amino]ethanol sulphate | — | $10^{-3}$ mol | — | — |
| 5-Methylpyrazolo[1,5-a]pyrimidine-3,7-diamine hydrochloride | — | — | $10^{-3}$ mol | — |
| 2-(4,5-Diaminopyrazol-1-yl)ethanol hydrochloride | — | — | — | $10^{-3}$ mol |
| Dye support (1) | (*) | (*) | (*) | (*) |
| Demineralized water qs | 100 g | 100 g | 100 g | 100 g |

(*) Dye support
(1) pH 9.5

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| $C_8$–$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 3.2 g |

Each composition is mixed at the time of use with an equal weight of 20-volumes aqueous hydrogen peroxide solution (6% by weight). A final pH of 9.5 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 8 | 9 | 10 | 11 |
|---|---|---|---|---|
| Shade observed | red-brown | brown | red-violet | Red |

Examples 12 to 15

Of Dyeing in Alkaline Medium

The dye compositions were prepared in the following proportions:

| Example | 12 | 13 | 14 | 15 |
|---|---|---|---|---|
| 6-Methoxy-N2-butyl-N2-methylpyridine-2,3-diamine | $10^{-3}$ mol | $10^{-3}$ mol | $10^{-3}$ mol | $10^{-3}$ mol |
| Benzene-1,4-diamine hydrochloride | $10^{-3}$ mol | — | — | — |
| 2-[(4-Aminophenyl) (2-hydroxyethyl)amino]ethanol sulphate | — | $10^{-3}$ mol | — | — |
| 5-Methylpyrazolo[1,5-a]pyrimidine-3,7-diamine hydrochloride | — | — | $10^{-3}$ mol | — |
| 2-(4,5-Diaminopyrazol-1-yl)ethanol hydrochloride | — | — | — | $10^{-3}$ mol |
| Dye support (1) | (*) | (*) | (*) | (*) |
| Demineralized water qs | 100 g | 100 g | 100 g | 100 g |

(*) Dye support (1) pH 9.5

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| $C_8$–$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 3.2 g |

Each composition is mixed at the time of use with an equal weight of 20-volumes aqueous hydrogen peroxide solution (6% by weight). A final pH of 9.5 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 12 | 13 | 14 | 15 |
|---|---|---|---|---|
| Shade observed | strong brown | grey | strong violet | red-brown |

Examples 16 to 21

Of Dyeing in Alkaline Medium

The dye compositions were prepared in the following proportions:

| Example | 16 | 17 | 18 | 19 | 20 | 21 |
|---|---|---|---|---|---|---|
| 6-Methoxy-N2-(3-aminopropyl)-N2-methylpyridine-2,3-diamine | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — | — |
| Benzene-1,4-diamine hydrochloride | — | $10^{-3}$ mol | — | — | — | — |
| 2-[(4-Aminophenyl) (2-hydroxyethyl)amino]ethanol sulphate | — | — | $10^{-3}$ mol | — | — | — |
| 2-Ethyl-5-methyl-2H-pyrazole-3,4-diamine hydrochloride | — | — | — | $10^{-3}$ mol | — | — |
| 5-Methylpyrazolo[1,5-a]pyrimidine-3,7-diamine hydrochloride | — | — | — | — | $10^{-3}$ mol | — |
| 2-(4,5-Diaminopyrazol-1-yl)ethanol hydrochloride | — | — | — | — | — | $10^{-3}$ mol |
| Dye support (1) | (*) | (*) | (*) | (*) | (*) | (*) |
| Demineralized water qs | 100 g | 100 g | 100 g | 100 g | 100 g | 100 g |

(*) Dye support (1) pH 9.5

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| $C_8$–$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 3.2 g |

Each composition is mixed at the time of use with an equal weight of 20-volumes aqueous hydrogen peroxide solution (6% by weight). A final pH of 9.5 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 16 | 17 | 18 | 19 | 20 | 21 |
|---|---|---|---|---|---|---|
| Shade observed | orange-brown | strong violet-grey | strong blue | grey | strong violet-grey | strong violet |

Examples 22 to 23

Of Dyeing in Alkaline Medium

The dye compositions were prepared in the following proportions:

| Example | 22 | 23 |
|---|---|---|
| 2-[(3-Amino-6-methoxy-2-pyridyl)ethylamino]ethanol | $10^{-3}$ mol | $10^{-3}$ mol |
| Benzene-1,4-diamine hydrochloride | $10^{-3}$ mol | — |

| Example | 22 | 23 |
|---|---|---|
| 5-Methylpyrazolo[1,5-a]pyrimidine-3,7-diamine hydrochloride | — | $10^{-3}$ mol |
| Dye support (1) | (*) | (*) |
| Demineralized water qs | 100 g | 100 g |

(*) Dye support
(1) pH 9.5

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| $C_8$–$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 3.2 g |

Each composition is mixed at the time of use with an equal weight of 20-volumes aqueous hydrogen peroxide solution (6% by weight). A final pH of 9.5 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 22 | 23 |
|---|---|---|
| Shade observed | orange-brown | red-violet |

Examples 24 to 25

Of Dyeing in Alkaline Medium

The dye compositions were prepared in the following proportions:

| Example | 24 | 25 |
|---|---|---|
| 6-Methoxy-N2,N2-dipropylpyridine-2,3-diamine | $10^{-3}$ mol | $10^{-3}$ mol |
| Benzene-1,4-diamine hydrochloride | $10^{-3}$ mol | — |
| 5-Methylpyrazolo[1,5-a]pyrimidine-3,7-diamine hydrochloride | — | $10^{-3}$ mol |
| Dye support (1) | (*) | (*) |
| Demineralized water qs | 100 g | 100 g |

(*) Dye support (1) pH 9.5

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| $C_8$–$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 3.2 g |

Each composition is mixed at the time of use with an equal weight of 20-volumes aqueous hydrogen peroxide solution (6% by weight). A final pH of 9.5 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 24 | 25 |
|---|---|---|
| Shade observed | red-brown | red-brown |

Examples 26 to 29

Of Dyeing in Alkaline Medium

The dye compositions were prepared in the following proportions:

| Example | 26 | 27 | 28 | 29 |
|---|---|---|---|---|
| 6-Methoxy-N2-butyl-N2-ethylpyridine-2,3-diamine | $10^{-3}$ mol | $10^{-3}$ mol | $10^{-3}$ mol | $10^{-3}$ mol |
| Benzene-1,4-diamine hydrochloride | $10^{-3}$ mol | — | — | — |
| 2-[(4-Aminophenyl) (2-hydroxyethyl)amino]ethanol sulphate | — | $10^{-3}$ mol | — | — |
| 5-Methylpyrazolo[1,5-a]pyrimidine-3,7-diamine hydrochloride | — | — | $10^{-3}$ mol | — |
| 2-(4,5-Diaminopyrazol-1-yl)ethanol hydrochloride | — | — | — | $10^{-3}$ mol |
| Dye support (1) | (*) | (*) | (*) | (*) |
| Demineralized water qs | 100 g | 100 g | 100 g | 100 g |

(*) Dye support (1) pH 9.5

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| $C_8$–$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 3.2 g |

Each composition is mixed at the time of use with an equal weight of 20-volumes aqueous hydrogen peroxide solution (6% by weight). A final pH of 9.5 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 26 | 27 | 28 | 29 |
|---|---|---|---|---|
| Shade observed | brown | grey | strong violet | red-grey |

Examples 30 to 35

Of Dyeing in Alkaline Medium

The dye compositions were prepared in the following proportions:

| Example | 30 | 31 | 32 | 33 | 34 | 35 |
|---|---|---|---|---|---|---|
| 6-Methoxy-N2-(2-amino-ethyl)-N2-isopropylpyridine-2,3-diamine | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — | — |
| Benzene-1,4-diamine hydrochloride | — | $10^{-3}$ mol | — | — | — | — |
| 2-[(4-Aminophenyl) (2-hydroxyethyl)amino] ethanol sulphate | — | — | $10^{-3}$ mol | — | — | — |
| 2-Ethyl-5-methyl-2H-pyrazole-3,4-diamine hydrochloride | — | — | — | $10^{-3}$ mol | — | — |
| 5-Methylpyrazolo[1,5-a]pyrimidine-3,7-diamine hydrochloride | — | — | — | — | $10^{-3}$ mol | — |
| 2-(4,5-Diaminopyrazol-1-yl) ethanol hydrochloride | — | — | — | — | — | $10^{-3}$ mol |
| Dye support (1) | (*) | (*) | (*) | (*) | (*) | (*) |
| Demineralized water qs | 100 g | 100 g | 100 g | 100 g | 100 g | 100 g |

(*) Dye support (1) pH 9.5

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| $C_8$–$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| NH$_4$Cl | 4.32 g |
| Aqueous ammonia containing 20% NH$_3$ | 3.2 g |

Each composition is mixed at the time of use with an equal weight of 20-volumes aqueous hydrogen peroxide solution (6% by weight). A final pH of 9.5 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 30 | 31 | 32 | 33 | 34 | 35 |
|---|---|---|---|---|---|---|
| Shade observed | orange | strong grey | strong blue-green grey | yellow-brown | strong violet-grey | strong violet |

Examples 36 to 39

Of Dyeing in Alkaline Medium

The dye compositions were prepared in the following proportions:

| Example | 36 | 37 | 38 | 39 |
|---|---|---|---|---|
| 6-Methoxy-N2-cyclohexyl-N2-methyl-pyridine-2,3-diamine | $10^{-3}$ mol | $10^{-3}$ mol | $10^{-3}$ mol | $10^{-3}$ mol |
| Benzene-1,4-diamine hydrochloride | $10^{-3}$ mol | — | — | — |
| 2-[(4-Aminophenyl) (2-hydroxyethyl)amino] ethanol sulphate | — | $10^{-3}$ mol | — | — |
| 5-Methylpyrazolo[1,5-a]pyrimidine-3,7-diamine hydrochloride | — | — | $10^{-3}$ mol | — |
| 2-(4,5-Diaminopyrazol-1-yl)ethanol hydrochloride | — | — | — | $10^{-3}$ mol |
| Dye support (1) | (*) | (*) | (*) | (*) |
| Demineralized water qs | 100 g | 100 g | 100 g | 100 g |

(*) Dye support (1) pH 9.5

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| $C_8$–$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| NH$_4$Cl | 4.32 g |
| Aqueous ammonia containing 20% NH$_3$ | 3.2 g |

Each composition is mixed at the time of use with an equal weight of 20-volumes aqueous hydrogen peroxide solution (6% by weight). A final pH of 9.5 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 36 | 37 | 38 | 39 |
|---|---|---|---|---|
| Shade observed | strong red-brown | grey | strong violet-grey | red-brown |

Examples 40 to 42

Of Dyeing in Alkaline Medium

The dye compositions were prepared in the following proportions:

| Example | 40 | 41 | 42 |
|---|---|---|---|
| 6-Methoxy-N2-methyl-N2-(6-methylaminohexyl) pyridine-2,3-diamine | $10^{-3}$ mol | $10^{-3}$ mol | $10^{-3}$ mol |
| Benzene-1,4-diamine hydrochloride | $10^{-3}$ mol | — | — |
| 2-[(4-Aminophenyl) (2-hydroxyethyl) amino]ethanol sulphate | — | $10^{-3}$ mol | — |
| 5-Methylpyrazolo[1,5-a]pyrimidine-3,7-diamine hydrochloride | — | — | $10^{-3}$ mol |
| Dye support (1) | (*) | (*) | (*) |
| Demineralized water qs | 100 g | 100 g | 100 g |

(*) Dye support (1) pH 9.5

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| $C_8$–$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 3.2 g |

Each composition is mixed at the time of use with an equal weight of 20-volumes aqueous hydrogen peroxide solution (6% by weight). A final pH of 9.5 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 40 | 41 | 42 |
|---|---|---|---|
| Shade observed | brown | grey | strong red-violet |

Examples 43 to 46

Of Dyeing in Alkaline Medium

The dye compositions were prepared in the following proportions:

| Example | 43 | 44 | 45 | 46 |
|---|---|---|---|---|
| 2-[(3-Amino-6-methoxy-2-pyridyl)pentyl-amino]ethanol | $10^{-3}$ mol | $10^{-3}$ mol | $10^{-3}$ mol | $10^{-3}$ mol |
| Benzene-1,4-diamine hydrochloride | $10^{-3}$ mol | — | — | — |
| 2-[(4-Aminophenyl) (2-hydroxyethyl) amino]ethanol sulphate | — | $10^{-3}$ mol | — | — |
| 5-Methylpyrazolo[1,5-a]pyrimidine-3,7-diamine hydrochloride | — | — | $10^{-3}$ mol | — |
| 2-(4,5-Diaminopyrazol-1-yl)ethanol hydrochloride | — | — | — | $10^{-3}$ mol |
| Dye support (1) | (*) | (*) | (*) | (*) |
| Demineralized water qs | 100 g | 100 g | 100 g | 100 g |

(*) Dye support (1) pH 9.5

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| $C_8$–$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 3.2 g |

Each composition is mixed at the time of use with an equal weight of 20-volumes aqueous hydrogen peroxide solution (6% by weight). A final pH of 9.5 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 43 | 44 | 45 | 46 |
|---|---|---|---|---|
| Shade observed | brown | green-yellow grey | strong red-violet grey | red-brown |

Examples 47 to 52

Of Dyeing in Alkaline Medium

The dye compositions were prepared in the following proportions:

| Example | 47 | 48 | 49 | 50 | 51 | 52 |
|---|---|---|---|---|---|---|
| 2-[(3-Amino-6-methoxy-2-pyridyl)cyclohexylamino]ethanol | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — | — |
| Benzene-1,4-diamine hydrochloride | — | $10^{-3}$ mol | — | — | — | — |
| 2-[(4-Aminophenyl) (2-hydroxyethyl)amino]ethanol sulphate | — | — | $10^{-3}$ mol | — | — | — |
| 2-Ethyl-5-methyl-2H-pyrazole-3,4-diamine hydrochloride | — | — | — | $10^{-3}$ mol | — | — |
| 5-Methylpyrazolo[1,5-a]pyrimidine-3,7-diamine hydrochloride | — | — | — | — | $10^{-3}$ mol | — |

-continued

| Example | 47 | 48 | 49 | 50 | 51 | 52 |
|---|---|---|---|---|---|---|
| 2-(4,5-Diaminopyrazol-1-yl)ethanol hydrochloride | — | — | — | — | — | $10^{-3}$ mol |
| Dye support (1) | (*) | (*) | (*) | (*) | (*) | (*) |
| Demineralized water qs | 100 g | 100 g | 100 g | 100 g | 100 g | 100 g |

(*) Dye support (1) pH 9.5

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| $C_8$–$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 3.2 g |

Each composition is mixed at the time of use with an equal weight of 20-volumes aqueous hydrogen peroxide solution (6% by weight). A final pH of 9.5 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 47 | 48 | 49 | 50 | 51 | 52 |
|---|---|---|---|---|---|---|
| Shade observed | red | strong grey | strong blue-green grey | grey | strong violet-grey | strong violet |

Examples 53 to 57

Of Dyeing in Alkaline Medium

The dye compositions were prepared in the following proportions:

| Example | 53 | 54 | 55 | 56 | 57 |
|---|---|---|---|---|---|
| 2-[(3-Amino-6-methoxy-2-pyridyl)(2-aminoethyl)-amino]ethanol | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — |
| Benzene-1,4-diamine hydrochloride | — | $10^{-3}$ mol | — | — | — |
| 2-[(4-Aminophenyl)(2-hydroxyethyl)amino]ethanol sulphate | — | — | $10^{-3}$ mol | — | — |
| 5-Methylpyrazolo[1,5-a]pyrimidine-3,7-diamine hydrochloride | — | — | — | $10^{-3}$ mol | — |
| 2-(4,5-Diaminopyrazol-1-yl)ethanol hydrochloride | — | — | — | — | $10^{-3}$ mol |
| Dye support (1) | (*) | (*) | (*) | (*) | (*) |
| Demineralized water qs | 100 g | 100 g | 100 g | 100 g | 100 g |

(*) Dye support (1) pH 9.5

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| $C_8$–$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 3.2 g |

Each composition is mixed at the time of use with an equal weight of 20-volumes aqueous hydrogen peroxide solution (6% by weight). A final pH of 9.5 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 53 | 54 | 55 | 56 | 57 |
|---|---|---|---|---|---|
| Shade observed | orange | strong grey | blue-green grey | strong violet-grey | violet-grey |

Examples 58 to 61

Of Dyeing in Alkaline Medium

The dye compositions were prepared in the following proportions:

| Example | 58 | 59 | 60 | 61 |
|---|---|---|---|---|
| 6-Methoxy-N2-cyclohexyl-N2-ethylpyridine-2,3-diamine | $10^{-3}$ mol | $10^{-3}$ mol | $10^{-3}$ mol | $10^{-3}$ mol |
| Benzene-1,4-diamine hydrochloride | $10^{-3}$ mol | — | — | — |
| 2-[(4-Aminophenyl)(2-hydroxyethyl)amino]ethanol sulphate | — | $10^{-3}$ mol | — | — |
| 5-Methylpyrazolo[1,5-a]pyrimidine-3,7-diamine hydrochloride | — | — | $10^{-3}$ mol | — |
| 2-(4,5-Diaminopyrazol-1-yl)ethanol hydrochloride | — | — | — | $10^{-3}$ mol |
| Dye support (1) | (*) | (*) | (*) | (*) |
| Demineralized water qs | 100 g | 100 g | 100 g | 100 g |

(*) Dye support (1) pH 9.5

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| $C_8$–$C_{10}$ alkyl polyglucoside as an aqueous 60% solution | 3.6 g AM |
| Benzyl alcohol | 2.0 g |

-continued

| | |
|---|---|
| Polyethylene glycol containing 8 ethylene oxide units | 3.0 g |
| NH$_4$Cl | 4.32 g |
| Aqueous ammonia containing 20% NH$_3$ | 3.2 g |

Each composition is mixed at the time of use with an equal weight of 20-volumes aqueous hydrogen peroxide solution (6% by weight). A final pH of 9.5 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 58 | 59 | 60 | 61 |
|---|---|---|---|---|
| Shade observed | red-brown | brown | red-grey | red |

Examples 62 to 68

Of Dyeing in Acidic Medium

The dye compositions were prepared in the following proportions:

| Example | 62 | 63 | 64 | 65 | 66 | 67 | 68 |
|---|---|---|---|---|---|---|---|
| 6-Methoxy-N2-ethyl-N2-methylpyridine-2,3-diamine | 10$^{-3}$ mol | 10$^{-3}$ mol | 10$^{-3}$ mol | 10$^{-3}$ mol | 10$^{-3}$ mol | 10$^{-3}$ mol | 10$^{-3}$ mol |
| 4-Aminophenol | 10$^{-3}$ mol | — | — | — | — | — | — |
| Benzene-1,4-diamine hydrochloride | — | 10$^{-3}$ mol | — | — | — | — | — |
| 2-[(4-Aminophenyl)(2-hydroxyethyl)amino]-ethanol sulphate | — | — | 10$^{-3}$ mol | — | — | — | — |
| Pyrimidine-2,4,5,6-tetraamine sulphate | — | — | — | 10$^{-3}$ mol | — | — | — |
| 2-Ethyl-5-methyl-2H-pyrazole-3,4-diamine hydrochloride | — | — | — | — | 10$^{-3}$ mol | — | — |
| 5-Methylpyrazolo[1,5-a]pyrimidine-3,7-diamine hydrochloride | — | — | — | — | — | 10$^{-3}$ mol | — |
| 2-(4,5-Diaminopyrazol-1-yl)ethanol hydrochloride | — | — | — | — | — | — | 10$^{-3}$ mol |
| Dye support (2) | (*) | (*) | (*) | (*) | (*) | (*) | (*) |
| Demineralized water qs | 100 g | 100 g | 100 g | 100 g | 100 g | 100 g | 100 g |

(*) Dye support (2) pH 7

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| Sodium metabisulphite as an aqueous 35% solution | 3.6 g AM |
| Benzyl alcohol | 2.0 g |

-continued

| | |
|---|---|
| Polyethylene glycol containing 8 ethylene oxide units | 3.0 g |
| KH$_2$PO$_4$ | 0.28 g |
| NaH$_2$PO$_4$ | 0.47 g |

Each composition is mixed at the time of use with an equal weight of 20-volumes aqueous hydrogen peroxide solution (6% by weight). A final pH of 7 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 62 | 63 | 64 | 65 | 66 | 67 | 68 |
|---|---|---|---|---|---|---|---|
| Shade observed | orange | strong brown | strong grey | yellow-brown | grey | strong grey | strong brown |

Examples 69 to 75

Of Dyeing in Acidic Medium

The dye compositions were prepared in the following proportions:

| Example | 69 | 70 | 71 | 72 | 73 | 74 | 75 |
|---|---|---|---|---|---|---|---|
| 6-Methoxy-N2-methyl-N2-propyl-pyridine-2,3-diamine | 10$^{-3}$ mol | 10$^{-3}$ mol | 10$^{-3}$ mol | 10$^{-3}$ mol | 10$^{-3}$ mol | 10$^{-3}$ mol | 10$^{-3}$ mol |
| 4-Aminophenol | 10$^{-3}$ mol | — | — | — | — | — | — |
| Benzene-1,4-diamine hydrochloride | — | 10$^{-3}$ mol | — | — | — | — | — |
| 2-[(4-Aminophenyl)(2-hydroxyethyl)amino]-ethanol sulphate | — | — | 10$^{-3}$ mol | — | — | — | — |
| Pyrimidine-2,4,5,6-tetraamine sulphate | — | — | — | 10$^{-3}$ mol | — | — | — |
| 2-Ethyl-5-methyl-2H-pyrazole-3,4-diamine hydrochloride | — | — | — | — | 10$^{-3}$ mol | — | — |
| 5-Methylpyrazolo[1,5-a]pyrimidine-3,7-diamine hydrochloride | — | — | — | — | — | 10$^{-3}$ mol | — |
| 2-(4,5-Diaminopyrazol-1-yl)ethanol hydrochloride | — | — | — | — | — | — | 10$^{-3}$ mol |
| Dye support (2) | (*) | (*) | (*) | (*) | (*) | (*) | (*) |
| Demineralized water qs | 100 g | 100 g | 100 g | 100 g | 100 g | 100 g | 100 g |

(*) Dye support (2) pH 7

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |

-continued

| | |
|---|---|
| Sodium metabisulphite as an aqueous 35% solution | 3.6 g AM |
| Benzyl alcohol | 2.0 g |
| Polyethylene glycol containing 8 ethylene oxide units | 3.0 g |
| $KH_2PO_4$ | 0.28 g |
| $NaH_2PO_4$ | 0.47 g |

Each composition is mixed at the time of use with an equal weight of 20-volumes aqueous hydrogen peroxide solution (6% by weight). A final pH of 7 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 69 | 70 | 71 | 72 | 73 | 74 | 75 |
|---|---|---|---|---|---|---|---|
| Shade observed | orange | strong blue-grey | strong blue-green | yellow | strong grey | strong grey | strong violet-grey |

Examples 76 to 82

Of Dyeing in Acidic Medium

The dye compositions were prepared in the following proportions:

| Example | 76 | 77 | 78 | 79 | 80 | 81 | 82 |
|---|---|---|---|---|---|---|---|
| 6-Methoxy-N2-butyl-N2-methyl-pyridine-2,3-diamine | $10^{-3}$ mol | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — | — | — |
| Benzene-1,4-diamine hydrochloride | — | $10^{-3}$ mol | — | — | — | — | — |
| 2-[(4-Aminophenyl)(2-hydroxyethyl)amino]-ethanol sulphate | — | — | $10^{-3}$ mol | — | — | — | — |
| Pyrimidine-2,4,5,6-tetraamine sulphate | — | — | — | $10^{-3}$ mol | — | — | — |
| 2-Ethyl-5-methyl-2H-pyrazole-3,4-diamine hydrochloride | — | — | — | — | $10^{-3}$ mol | — | — |
| 5-Methylpyrazolo[1,5-a]pyrimidine-3,7-diamine hydrochloride | — | — | — | — | — | $10^{-3}$ mol | — |
| 2-(4,5-Diaminopyrazol-1-yl)ethanol hydrochloride | — | — | — | — | — | — | $10^{-3}$ mol |
| Dye support (2) | (*) | (*) | (*) | (*) | (*) | (*) | (*) |
| Demineralized water qs | 100 g | 100 g | 100 g | 100 g | 100 g | 100 g | 100 g |

(*) Dye support (2) pH 7

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| Sodium metabisulphite as an aqueous 35% solution | 3.6 g AM |
| Benzyl alcohol | 2.0 g |
| Polyethylene glycol containing 8 ethylene oxide units | 3.0 g |
| $KH_2PO_4$ | 0.28 g |
| $NaH_2PO_4$ | 0.47 g |

Each composition is mixed at the time of use with an equal weight of 20-volumes aqueous hydrogen peroxide solution (6% by weight). A final pH of 7 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 76 | 77 | 78 | 79 | 80 | 81 | 82 |
|---|---|---|---|---|---|---|---|
| Shade observed | orange | strong blue-grey | strong blue-green | yellow-brown | grey | strong voilet-grey | strong violet-grey |

Examples 83 to 89

Of Dyeing in Acidic Medium

The dye compositions were prepared in the following proportions:

| Example | 83 | 84 | 85 | 86 | 87 | 88 | 89 |
|---|---|---|---|---|---|---|---|
| 6-Methoxy-N2-(3-aminopropyl)-N2-methylpyridine-2,3-diamine | $10^{-3}$ mol | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — | — | — |
| Benzene-1,4-diamine hydrochloride | — | $10^{-3}$ mol | — | — | — | — | — |
| 2-[(4-Aminophenyl)(2-hydroxyethyl)amino]-ethanol sulphate | — | — | $10^{-3}$ mol | — | — | — | — |
| Pyrimidine-2,4,5,6-tetraamine sulphate | — | — | — | $10^{-3}$ mol | — | — | — |
| 2-Ethyl-5-methyl-2H-pyrazole-3,4-diamine hydrochloride | — | — | — | — | $10^{-3}$ mol | — | — |
| 5-Methylpyrazolo[1,5-a]pyrimidine-3,7-diamine hydrochloride | — | — | — | — | — | $10^{-3}$ mol | — |
| 2-(4,5-Diaminopyrazol-1-yl)ethanol hydrochloride | — | — | — | — | — | — | $10^{-3}$ mol |
| Dye support (2) | (*) | (*) | (*) | (*) | (*) | (*) | (*) |
| Demineralized water qs | 100 g | 100 g | 100 g | 100 g | 100 g | 100 g | 100 g |

(*) Dye support (2) pH 7

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| Sodium metabisulphite as an aqueous 35% solution | 3.6 g AM |
| Benzyl alcohol | 2.0 g |
| Polyethylene glycol containing 8 ethylene oxide units | 3.0 g |
| $KH_2PO_4$ | 0.28 g |
| $NaH_2PO_4$ | 0.47 g |

Each composition is mixed at the time of use with an equal weight of 20-volumes aqueous hydrogen peroxide solution (6% by weight). A final pH of 7 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 83 | 84 | 85 | 86 | 87 | 88 | 89 |
|---|---|---|---|---|---|---|---|
| Shade observed | strong yellow-brown | strong grey | strong blue-grey | strong grey | strong grey | strong grey | strong grey |

Examples 90 to 94

Of Dyeing in Acidic Medium

The dye compositions were prepared in the following proportions:

| Example | 90 | 91 | 92 | 93 | 94 |
|---|---|---|---|---|---|
| 2-[(3-Amino-6-methoxy-2-pyridyl)ethylamino]ethanol | $10^{-3}$ mol | $10^{-3}$ mol | $10^{-3}$ mol | $10^{-3}$ mol | $10^{-3}$ mol |
| Benzene-1,4-diamine hydrochloride | $10^{-3}$ mol | — | — | — | — |
| 2-[(4-Aminophenyl) (2-hydroxyethyl)amino]ethanol sulphate | — | $10^{-3}$ mol | — | — | — |
| 2-Ethyl-5-methyl-2H-pyrazole-3,4-diamine hydrochloride | — | — | $10^{-3}$ mol | — | — |
| 5-Methylpyrazolo[1,5-a]pyrimidine-3,7-diamine hydrochloride | — | — | — | $10^{-3}$ mol | — |
| 2-(4,5-Diaminopyrazol-1-yl)ethanol hydrochloride | — | — | — | — | $10^{-3}$ mol |
| Dye support (2) | (*) | (*) | (*) | (*) | (*) |
| Demineralized water qs | 100 g | 100 g | 100 g | 100 g | 100 g |

(*) Dye support (2) pH 7

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| Sodium metabisulphite as an aqueous 35% solution | 3.6 g AM |
| Benzyl alcohol | 2.0 g |
| Polyethylene glycol containing 8 ethylene oxide units | 3.0 g |
| $KH_2PO_4$ | 0.28 g |
| $NaH_2PO_4$ | 0.47 g |

Each composition is mixed at the time of use with an equal weight of 20-volumes aqueous hydrogen peroxide solution (6% by weight). A final pH of 7 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 90 | 91 | 92 | 93 | 94 |
|---|---|---|---|---|---|
| Shade observed | strong grey-blue | blue-green | brown | strong violet-grey | strong violet |

Examples 95 to 99

Of Dyeing in Acidic Medium

The dye compositions were prepared in the following proportions:

| Example | 95 | 96 | 97 | 98 | 99 |
|---|---|---|---|---|---|
| 6-Methoxy-N2,N2-dipropylpyridine-2,3-diamine | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — |
| Benzene-1,4-diamine hydrochloride | — | $10^{-3}$ mol | — | — | — |
| 2-[(4-Aminophenyl) (2-hydroxyethyl)amino]ethanol sulphate | — | — | $10^{-3}$ mol | — | — |
| 5-Methylpyrazolo[1,5-a]pyrimidine-3,7-diamine hydrochloride | — | — | — | $10^{-3}$ mol | — |
| 2-(4,5-Diaminopyrazol-1-yl)ethanol hydrochloride | — | — | — | — | $10^{-3}$ mol |
| Dye support (2) | (*) | (*) | (*) | (*) | (*) |
| Demineralized water qs | 100 g | 100 g | 100 g | 100 g | 100 g |

(*) Dye support (2) pH 7

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| Sodium metabisulphite as an aqueous 35% solution | 3.6 g AM |
| Benzyl alcohol | 2.0 g |
| Polyethylene glycol containing 8 ethylene oxide units | 3.0 g |
| $KH_2PO_4$ | 0.28 g |
| $NaH_2PO_4$ | 0.47 g |

Each composition is mixed at the time of use with an equal weight of 20-volumes aqueous hydrogen peroxide solution (6% by weight). A final pH of 7 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 95 | 96 | 97 | 98 | 99 |
|---|---|---|---|---|---|
| Shade observed | orange | strong grey | strong blue-green grey | strong violet-grey | red |

| Example | 100 | 101 | 102 | 103 | 104 | 105 | 106 |
|---|---|---|---|---|---|---|---|
| Shade observed | orange | strong blue-grey | strong blue-green | yellow-brown | grey | strong violet-grey | strong violet-grey |

Examples 100 to 106

Of Dyeing in Acidic Medium

The dye compositions were prepared in the following proportions:

| Example | 100 | 101 | 102 | 103 | 104 | 105 | 106 |
|---|---|---|---|---|---|---|---|
| 6-Methoxy-N2-methyl-N2-(6-methyl-aminohexyl)pyridine-2,3-diamine | $10^{-3}$ mol | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — | — | — |
| Benzene-1,4-diamine hydrochloride | — | $10^{-3}$ mol | — | — | — | — | — |
| 2-[(4-Aminophenyl)(2-hydroxyethyl)amino]-ethanol sulphate | — | — | $10^{-3}$ mol | — | — | — | — |
| Pyrimidine-2,4,5,6-tetraamine sulphate | — | — | — | $10^{-3}$ mol | — | — | — |
| 2-Ethyl-5-methyl-2H-pyrazole-3,4-diamine hydrochloride | — | — | — | — | $10^{-3}$ mol | — | — |
| 5-Methylpyrazolo[1,5-a]pyrimidine-3,7-diamine hydrochloride | — | — | — | — | — | $10^{-3}$ mol | — |
| 2-(4,5-Diaminopyrazol-1-yl)ethanol hydrochloride | — | — | — | — | — | — | $10^{-3}$ mol |
| Dye support (2) | (*) | (*) | (*) | (*) | (*) | (*) | (*) |
| Demineralized water qs | 100 g | 100 g | 100 g | 100 g | 100 g | 100 g | 100 g |

(*) Dye support (2) pH 7

Examples 107 to 113

Of Dyeing in Acidic Medium

The dye compositions were prepared in the following proportions:

| Example | 107 | 108 | 109 | 110 | 111 | 112 | 113 |
|---|---|---|---|---|---|---|---|
| 6-Methoxy-N2-(2-aminoethyl)-N2-isopropylpyridine-2,3-diamine | $10^{-3}$ mol | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — | — | — |
| Benzene-1,4-diamine hydrochloride | — | $10^{-3}$ mol | — | — | — | — | — |
| 2-[(4-Aminophenyl)(2-hydroxyethyl)amino]-ethanol sulphate | — | — | $10^{-3}$ mol | — | — | — | — |
| Pyrimidine-2,4,5,6-tetraamine sulphate | — | — | — | $10^{-3}$ mol | — | — | — |
| 2-Ethyl-5-methyl-2H-pyrazole-3,4-diamine hydrochloride | — | — | — | — | $10^{-3}$ mol | — | — |
| 5-Methylpyrazolo[1,5-a]pyrimidine-3,7-diamine hydrochloride | — | — | — | — | — | $10^{-3}$ mol | — |
| 2-(4,5-Diaminopyrazol-1-yl)ethanol hydrochloride | — | — | — | — | — | — | $10^{-3}$ mol |
| Dye support (2) | (*) | (*) | (*) | (*) | (*) | (*) | (*) |
| Demineralized water qs | 100 g | 100 g | 100 g | 100 g | 100 g | 100 g | 100 g |

(*) Dye support (2) pH 7

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| Sodium metabisulphite as an aqueous 35% solution | 3.6 g AM |
| Benzyl alcohol | 2.0 g |
| Polyethylene glycol containing 8 ethylene oxide units | 3.0 g |
| $KH_2PO_4$ | 0.28 g |
| $NaH_2PO_4$ | 0.47 g |

Each composition is mixed at the time of use with an equal weight of 20-volumes aqueous hydrogen peroxide solution (6% by weight). A final pH of 7 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 107 | 108 | 109 | 110 | 111 | 112 | 113 |
|---|---|---|---|---|---|---|---|
| Shade observed | strong yellow-brown | strong grey | strong grey | Grey | grey | strong grey | strong grey |

Examples 114 to 120

Dyeing in Acidic Medium

The dye compositions were prepared in the following proportions:

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| Sodium metabisulphite as an aqueous 35% solution | 3.6 g AM |
| Benzyl alcohol | 2.0 g |
| Polyethylene glycol containing 8 ethylene oxide units | 3.0 g |
| $KH_2PO_4$ | 0.28 g |
| $NaH_2PO_4$ | 0.47 g |

Each composition is mixed at the time of use with an equal weight of 20-volumes aqueous hydrogen peroxide solution (6% by weight). A final pH of 7 is obtained.

Each mixture obtained is applied to grey hair containing 90% white hairs. After a leave-in time of 30 minutes, the hair is rinsed, washed with a standard shampoo, rinsed again and then dried.

| Example | 114 | 115 | 116 | 117 | 118 | 119 | 120 |
|---|---|---|---|---|---|---|---|
| 6-Methoxy-N2-cyclohexyl-N2-methylpyridine-2,3-diamine | $10^{-3}$ mol | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — | — | — |
| Benzene-1,4-diamine hydrochloride | — | $10^{-3}$ mol | — | — | — | — | — |
| 2-[(4-Aminophenyl) (2-hydroxyethyl)amino]-ethanol sulphate | — | — | $10^{-3}$ mol | — | — | — | — |
| Pyrimidine-2,4,5,6-tetraamine sulphate | — | — | — | $10^{-3}$ mol | — | — | — |
| 2-Ethyl-5-methyl-2H-pyrazole-3,4-diamine hydrochloride | — | — | — | — | $10^{-3}$ mol | — | — |
| 5-Methylpyrazolo[1,5-a]pyrimidine-3,7-diamine hydrochloride | — | — | — | — | — | $10^{-3}$ mol | — |
| 2-(4,5-Diaminopyrazol-1-yl)ethanol hydrochloride | — | — | — | — | — | — | $10^{-3}$ mol |
| Dye support (2) | (*) | (*) | (*) | (*) | (*) | (*) | (*) |
| Demineralized water qs | 100 g | 100 g | 100 g | 100 g | 100 g | 100 g | 100 g |

(*) Dye support (2) pH 7

The following dyeing results were obtained.

| Example | 114 | 115 | 116 | 117 | 118 | 119 | 120 |
|---|---|---|---|---|---|---|---|
| Shade observed | orange | strong grey | strong blue-green | yellow-brown | brown | strong violet-grey | strong violet-grey |

Examples 121 to 127

Dyeing in Acidic Medium

The dye compositions were prepared in the following proportions:

| Example | 121 | 122 | 123 | 124 | 125 | 126 | 127 |
|---|---|---|---|---|---|---|---|
| 6-Methoxy-N2-benzyl-N2-methylpyridine-2,3-diamine | $10^{-3}$ mol | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — | — | — |
| Benzene-1,4-diamine hydrochloride | — | $10^{-3}$ mol | — | — | — | — | — |
| 2-[(4-Aminophenyl) (2-hydroxyethyl)amino]-ethanol sulphate | — | — | $10^{-3}$ mol | — | — | — | — |
| Pyrimidine-2,4,5,6-tetraamine sulphate | — | — | — | $10^{-3}$ mol | — | — | — |
| 2-Ethyl-5-methyl-2H-pyrazole-3,4-diamine hydrochloride | — | — | — | — | $10^{-3}$ mol | — | — |
| 5-Methylpyrazolo[1,5-a]pyrimidine-3,7-diamine hydrochloride | — | — | — | — | — | $10^{-3}$ mol | — |
| 2-(4,5-Diaminopyrazol-1-yl)ethanol hydrochloride | — | — | — | — | — | — | $10^{-3}$ mol |
| Dye support (2) | (*) | (*) | (*) | (*) | (*) | (*) | (*) |
| Demineralized water qs | 100 g | 100 g | 100 g | 100 g | 100 g | 100 g | 100 g |

(*) Dye support (2) pH 7

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| Sodium metabisulphite as an aqueous 35% solution | 3.6 g AM |
| Benzyl alcohol | 2.0 g |
| Polyethylene glycol containing 8 ethylene oxide units | 3.0 g |
| $KH_2PO_4$ | 0.28 g |
| $NaH_2PO_4$ | 0.47 g |

Each composition is mixed at the time of use with an equal weight of 20-volumes aqueous hydrogen peroxide solution (6% by weight). A final pH of 7 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 121 | 122 | 123 | 124 | 125 | 126 | 127 |
|---|---|---|---|---|---|---|---|
| Shade observed | orange | strong orange | strong orange | strong yellow | strong yellow | strong yellow-brown | strong orange-brown |

Examples 128 to 134

Of Dyeing in Acidic Medium

The dye compositions were prepared in the following proportions:

| Example | 128 | 129 | 130 | 131 | 132 | 133 | 134 |
|---|---|---|---|---|---|---|---|
| 6-Methoxy-N2-cyclohexyl-N2-ethylpyridine-2,3-diamine | $10^{-3}$ mol | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — | — | — |
| Benzene-1,4-diamine hydrochloride | — | $10^{-3}$ mol | — | — | — | — | — |
| 2-[(4-Aminophenyl) (2-hydroxyethyl)amino]-ethanol sulphate | — | — | $10^{-3}$ mol | — | — | — | — |
| Pyrimidine-2,4,5,6-tetraamine sulphate | — | — | — | $10^{-3}$ mol | — | — | — |
| 2-Ethyl-5-methyl-2H-pyrazole-3,4-diamine hydrochloride | — | — | — | — | $10^{-3}$ mol | — | — |
| 5-Methylpyrazolo[1,5-a]pyrimidine-3,7-diamine hydrochloride | — | — | — | — | — | $10^{-3}$ mol | — |
| 2-(4,5-Diaminopyrazol-1-yl)ethanol hydrochloride | — | — | — | — | — | — | $10^{-3}$ mol |
| Dye support (2) | (*) | (*) | (*) | (*) | (*) | (*) | (*) |
| Demineralized water qs | 100 g | 100 g | 100 g | 100 g | 100 g | 100 g | 100 g |

(*) Dye support (2) pH 7

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| Sodium metabisulphite as an aqueous 35% solution | 3.6 g AM |
| Benzyl alcohol | 2.0 g |
| Polyethylene glycol containing 8 ethylene oxide units | 3.0 g |
| $KH_2PO_4$ | 0.28 g |
| $NaH_2PO_4$ | 0.47 g |

Each composition is mixed at the time of use with an equal weight of 20-volumes aqueous hydrogen peroxide solution (6% by weight). A final pH of 7 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 128 | 129 | 130 | 131 | 132 | 133 | 134 |
|---|---|---|---|---|---|---|---|
| Shade observed | orange | strong red-brown | strong grey | yellow-brown | brown | strong grey | strong brown |

Examples 135 to 141

Of Dyeing in Acidic Medium

The dye compositions were prepared in the following proportions:

| Example | 135 | 136 | 137 | 138 | 139 | 140 | 141 |
|---|---|---|---|---|---|---|---|
| 2-[(3-Amino-6-methoxy-2-pyridyl)pentylamino]ethanol | $10^{-3}$ mol | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — | — | — |
| Benzene-1,4-diamine hydrochloride | — | $10^{-3}$ mol | — | — | — | — | — |
| 2-[(4-Aminophenyl) (2-hydroxyethyl)amino]-ethanol sulphate | — | — | $10^{-3}$ mol | — | — | — | — |
| Pyrimidine-2,4,5,6-tetraamine sulphate | — | — | — | $10^{-3}$ mol | — | — | — |
| 2-Ethyl-5-methyl-2H-pyrazole-3,4-diamine hydrochloride | — | — | — | — | $10^{-3}$ mol | — | — |
| 5-Methylpyrazolo[1,5-a]pyrimidine-3,7-diamine hydrochloride | — | — | — | — | — | $10^{-3}$ mol | — |
| 2-(4,5-Diaminopyrazol-1-yl)ethanol hydrochloride | — | — | — | — | — | — | $10^{-3}$ mol |
| Dye support (2) | (*) | (*) | (*) | (*) | (*) | (*) | (*) |
| Demineralized water qs | 100 g | 100 g | 100 g | 100 g | 100 g | 100 g | 100 g |

(*) Dye support (2) pH 7

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| Sodium metabisulphite as an aqueous 35% solution | 3.6 g AM |
| Benzyl alcohol | 2.0 g |
| Polyethylene glycol containing 8 ethylene oxide units | 3.0 g |
| $KH_2PO_4$ | 0.28 g |
| $NaH_2PO_4$ | 0.47 g |

Each composition is mixed at the time of use with an equal weight of 20-volumes aqueous hydrogen peroxide solution (6% by weight). A final pH of 7 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 135 | 136 | 137 | 138 | 139 | 140 | 141 |
|---|---|---|---|---|---|---|---|
| Shade observed | yellow | brown | strong blue-green grey | yellow-brown | grey | strong violet-grey | strong violet-grey |

Examples 142 to 148

Of Dyeing in Acidic Medium

The dye compositions were prepared in the following proportions:

| Example | 142 | 143 | 144 | 145 | 146 | 147 | 148 |
|---|---|---|---|---|---|---|---|
| 2-[(3-Amino-6-methoxy-2-pyridyl)cyclohexylamino]ethanol | $10^{-3}$ mol | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — | — | — |
| Benzene-1,4-diamine hydrochloride | — | $10^{-3}$ mol | — | — | — | — | — |
| 2-[(4-Aminophenyl) (2-hydroxyethyl)amino]-ethanol sulphate | — | — | $10^{-3}$ mol | — | — | — | — |
| Pyrimidine-2,4,5,6-tetraamine sulphate | — | — | — | $10^{-3}$ mol | — | — | — |
| 2-Ethyl-5-methyl-2H-pyrazole-3,4-diamine hydrochloride | — | — | — | — | $10^{-3}$ mol | — | — |
| 5-Methylpyrazolo[1,5-a]pyrimidine-3,7-diamine hydrochloride | — | — | — | — | — | $10^{-3}$ mol | — |
| 2-(4,5-Diaminopyrazol-1-yl)ethanol hydrochloride | — | — | — | — | — | — | $10^{-3}$ mol |
| Dye support (2) | (*) | (*) | (*) | (*) | (*) | (*) | (*) |
| Demineralized water qs | 100 g | 100 g | 100 g | 100 g | 100 g | 100 g | 100 g |

(*) Dye support (2) pH 7

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| Sodium metabisulphite as an aqueous 35% solution | 3.6 g AM |
| Benzyl alcohol | 2.0 g |
| Polyethylene glycol containing 8 ethylene oxide units | 3.0 g |
| $KH_2PO_4$ | 0.28 g |
| $NaH_2PO_4$ | 0.47 g |

Each composition is mixed at the time of use with an equal weight of 20-volumes aqueous hydrogen peroxide solution (6% by weight). A final pH of 7 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 142 | 143 | 144 | 145 | 146 | 147 | 148 |
|---|---|---|---|---|---|---|---|
| Shade observed | orange | red-brown | strong grey | yellow-brown | green-yellow grey | strong grey | strong brown |

Examples 149 to 155

Of Dyeing in Acidic Medium

The dye compositions were prepared in the following proportions:

| Example | 149 | 150 | 151 | 152 | 153 | 154 | 155 |
|---|---|---|---|---|---|---|---|
| 2-[(3-Amino-6-methoxy-2-pyridyl) (2-aminoethyl)amino]ethanol | $10^{-3}$ mol | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — | — | — |
| Benzene-1,4-diamine hydrochloride | — | $10^{-3}$ mol | — | — | — | — | — |
| 2-[(4-Aminophenyl) (2-hydroxyethyl)amino]-ethanol sulphate | — | — | $10^{-3}$ mol | — | — | — | — |
| Pyrimidine-2,4,5,6-tetraamine sulphate | — | — | — | $10^{-3}$ mol | — | — | — |
| 2-Ethyl-5-methyl-2H-pyrazole-3,4-diamine hydrochloride | — | — | — | — | $10^{-3}$ mol | — | — |
| 5-Methylpyrazolo[1,5-a]pyrimidine-3,7-diamine hydrochloride | — | — | — | — | — | $10^{-3}$ mol | — |
| 2-(4,5-Diaminopyrazol-1-yl)ethanol hydrochloride | — | — | — | — | — | — | $10^{-3}$ mol |
| Dye support (2) | (*) | (*) | (*) | (*) | (*) | (*) | (*) |
| Demineralized water qs | 100 g | 100 g | 100 g | 100 g | 100 g | 100 g | 100 g |

(*) Dye support (2) pH 7

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| Sodium metabisulphite as an aqueous 35% solution | 3.6 g AM |
| Benzyl alcohol | 2.0 g |
| Polyethylene glycol containing 8 ethylene oxide units | 3.0 g |
| KH$_2$PO$_4$ | 0.28 g |
| NaH$_2$PO$_4$ | 0.47 g |

Each composition is mixed at the time of use with an equal weight of 20-volumes aqueous hydrogen peroxide solution (6% by weight). A final pH of 7 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 149 | 150 | 151 | 152 | 153 | 154 | 155 |
|---|---|---|---|---|---|---|---|
| Shade observed | orange-brown | strong grey | strong blue-grey | grey | grey | strong grey | strong grey |

Examples 156 to 161

Of Dyeing in Acidic Medium

The dye compositions were prepared in the following proportions:

| Example | 156 | 157 | 158 | 159 | 160 | 161 |
|---|---|---|---|---|---|---|
| 6-Methoxy-N2-butyl-N2-ethylpyridine-2,3-diamine | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — | — |
| Benzene-1,4-diamine hydrochloride | — | $10^{-3}$ mol | — | — | — | — |
| 2-[(4-Aminophenyl) (2-hydroxyethyl)amino]-ethanol sulphate | — | — | $10^{-3}$ mol | — | — | — |
| 2-Ethyl-5-methyl-2H-pyrazole-3,4-diamine hydrochloride | — | — | — | $10^{-3}$ mol | — | — |
| 5-Methylpyrazolo[1,5-a]pyrimidine-3,7-diamine hydrochloride | — | — | — | — | $10^{-3}$ mol | — |
| 2-(4,5-Diaminopyrazol-1-yl)ethanol hydrochloride | — | — | — | — | — | $10^{-3}$ mol |
| Dye support (2) | (*) | (*) | (*) | (*) | (*) | (*) |
| Demineralized water qs | 100 g | 100 g | 100 g | 100 g | 100 g | 100 g |

(*) Dye support (2) pH 7

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| Sodium metabisulphite as an aqueous 35% solution | 3.6 g AM |
| Benzyl alcohol | 2.0 g |
| Polyethylene glycol containing 8 ethylene oxide units | 3.0 g |
| $KH_2PO_4$ | 0.28 g |
| $NaH_2PO_4$ | 0.47 g |

Each composition is mixed at the time of use with an equal weight of 20-volumes aqueous hydrogen peroxide solution (6% by weight). A final pH of 7 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| Example | 156 | 157 | 158 | 159 | 160 | 161 |
|---|---|---|---|---|---|---|
| Shade observed | orange-brown | strong blue-grey | strong blue-green | violet-grey | strong violet-grey | strong violet |

The invention claimed is:

1. A dye composition comprising, in a medium that is suitable for dyeing:
   at least one oxidation base, and
   at least one 6-alkoxy-2,3-diaminopyridine coupler of formula (I), or at least one addition salt thereof:

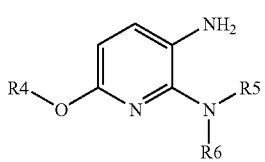

wherein:
   $R_4$ is chosen from linear and branched $C_1$–$C_4$ alkyl radicals optionally substituted with at least one radical chosen from hydroxyl, $C_1$–$C_2$ alkoxy, and $NR_7R_8$ radicals wherein $R_7$ and $R_8$ are chosen from hydrogen atoms, $C_1$–$C_4$ alkyl, $C_2$–$C_6$ (poly)hydroxyalkyl, $C_2$–$C_6$ (poly)aminoalkyl, and $C_2$–$C_6$ aminohydroxyalkyl radicals;
   $R_5$ is chosen from linear and branched $C_1$–$C_6$ alkyl radicals optionally substituted with at least one radical chosen from $C_1$–$C_2$ alkoxy, hydroxyl, carboxyl, sulphonic (—$SO_3H$), and $NR_9R_{10}$ radicals; acylaminoethyl radicals; and 2-(2-hydroxyethyloxy)ethyl radicals; and
   $R_6$ is chosen from linear and branched $C_1$–$C_4$ alkyl radicals substituted with at least one radical chosen from hydroxyl, $C_1$–$C_2$ alkoxy, amino, $C_1$–$C_2$ (di)alkylamino, carboxyl, acylamino, (di)hydroxyalkylamino radicals; and 2-(2-hydroxyethyloxy)ethyl radicals;

wherein $R_9$ and $R_{10}$, which are independent of each other, are chosen from hydrogen atoms and $C_1$–$C_4$ alkyl radicals optionally substituted with at least one radical chosen from hydroxyl, amino, monoalkylamino, dialkylamino, alkoxy, and acylamino radicals.

2. The dye composition according to claim 1, wherein $R_5$ is chosen from $C_1$–$C_4$ alkyl radicals optionally substituted with at least one radical chosen from hydroxyl, $C_1$–$C_2$ alkoxy, amino, $C_1$–$C_2$ (di)alkylamino, carboxyl and $C_1$–$C_2$ (di)hydroxyalkylamino radicals; 2-acylaminoethyl radicals; and 2-(2-hydroxyethyloxy)ethyl radicals.

3. The dye composition according to claim 2, wherein $R_5$ is chosen from methyl, ethyl, propyl, 2-hydroxyethyl, 2-aminoethyl, 2-carboxyethyl, 2-acylaminoethyl, 2-hydroxypropyl, 3-hydroxypropyl, 3-aminopropyl, 2-N,N-dimethylaminoethyl, 2-N-methylaminoethyl, 2-(2-hydroxyethylamino)ethyl, and 2-(2-hydroxyethyloxy)ethyl radicals.

4. The dye composition according to claim 1, wherein $R_6$ is chosen from 2-hydroxyethyl, 2-aminoethyl, 2-carboxyethyl, 2-acylaminoethyl, 2-hydroxypropyl, 3-hydroxypropyl, 3-aminopropyl, 2-N,N-dimethylaminoethyl, 2-N-methylaminoethyl, 2-(2-hydroxyethylamino)ethyl, and 2-(2-hydroxyethyloxy)ethyl radicals.

5. The dye composition according to claim 1, wherein $R_4$ is chosen from $C_1$–$C_4$ alkyl radicals optionally substituted with at least one radical chosen from hydroxyl and $C_1$–$C_2$ alkoxy radicals.

6. The dye composition according to claim 5, wherein $R_4$ is chosen from $C_1$–$C_4$ alkyl radicals.

7. The dye composition according to claim 6, wherein $R_5$ is an alkyl radical and $R_6$ is an alkyl radical substituted with at least one hydroxyl.

8. The dye composition according to claim 6, wherein $R_5$ and $R_6$ are chosen from alkyl radicals substituted with at least one hydroxyl.

9. The dye composition according to claim 1, wherein the compound of formula (I) is chosen from:
   2-[(3-amino-6-methoxy-2-pyridyl)methylamino]ethanol;
   2-[(3-amino-6-methoxy-2-pyridyl)butylamino]ethanol;
   2-[(3-amino-6-methoxy-2-pyridyl)(2-hydroxyethyl)amino]ethanol;
   3-[(3-amino-6-methoxy-2-pyridyl)methylamino]propane-1,2-diol;
   6-methoxy-N2,N2-bis(2-methoxyethyl)pyridine-2,3-diamine;
   6-methoxy-N2-(3-aminopropyl)-N2-methylpyridine-2,3-diamine;
   2-[(3-amino-6-methoxy-2-pyridyl)ethylamino]ethanol;
   6-methoxy-N2-(2-aminoethyl)-N2-isopropylpyridine-2,3-diamine;
   6-methoxy-N2-cyclohexyl-N2-methylpyridine-2,3-diamine;
   2-[(3-amino-6-methoxy-2-pyridyl)(3-aminopropyl)amino]ethanol;
   6-methoxy-N2-cyclohexyl-N2-ethylpyridine-2,3-diamine;
   2-[(3-amino-6-methoxy-2-pyridyl)pentylamino]ethanol;
   2-[(3-amino-6-methoxy-2-pyridyl)cyclohexylamino]ethanol;
   2-[(3-amino-6-methoxy-2-pyridyl)(2-aminoethyl)amino]ethanol;
   6-methoxy-N2-methyl-N2-(6-methylaminohexyl)pyridine-2,3-diamine;
   and the addition salts thereof.

10. The dye composition according to claim 1, wherein the at least one oxidation base is chosen from para-phenylenediamines, bis(phenyl)alkylenediamines, para-aminophenols, bis-para-aminophenols, ortho-aminophenols, heterocyclic bases, and the addition salts thereof.

11. The dye composition according to claim 1, wherein the at least one oxidation base is present in an amount ranging from 0.001% to 10% by weight, relative to the total weight of the dye composition, and wherein when more than one oxidation base is present, each oxidation base is present in said amount.

12. The dye composition according to claim 11, wherein the at least one oxidation base is present in an amount ranging from 0.005% to 6% by weight, relative to the total weight of the dye composition.

13. The dye composition according to claim 1, further comprising at least one additional coupler chosen from meta-phenylenediamines, meta-aminophenols, meta-diphenols, naphthalene-based couplers heterocyclic couplers, and the addition salts thereof, other than the at least one coupler of formula (I).

14. The dye composition according to claim 13, wherein for the at least one coupler of formula (I) and for the at least one additional coupler, if present, each coupler is present in the dye composition in an amount ranging from 0.001% to 10% by weight, relative to the total weight of the dye composition.

15. The dye composition according to claim 14, wherein the at least one coupler of formula (I) and for the at least one additional coupler, if present, each coupler is present in the dye composition in an amount ranging from 0.005% to 6% by weight, relative to the total weight of the dye composition.

16. The dye composition according to claim 1, wherein the dyeing medium is a cosmetic medium that is suitable for dyeing keratin fibers.

17. The dye composition according to claim 1, further comprising an oxidizing agent.

18. A process for the oxidation dyeing of keratin fibers comprising applying to the fibers, in the presence of an oxidizing agent, for a time that is sufficient to allow a desired color to be obtained, a dye composition comprising, in a medium that is suitable for dyeing:
at least one oxidation base, and
at least one 6-alkoxy-2,3-diaminopyridine coupler of formula (I), or at least one addition salt thereof:

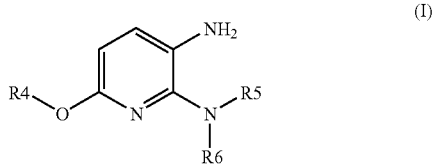

wherein:
$R_4$ is chosen from linear and branched $C_1$–$C_4$ alkyl radicals optionally substituted with at least one radical chosen from hydroxyl, $C_1$–$C_2$ alkoxy, and $NR_7R_8$ radicals wherein $R_7$ and $R_8$ are chosen from hydrogen atoms, $C_1$–$C_4$ alkyl, $C_2$–$C_6$ (poly)hydroxyalkyl, $C_2$–$C_6$ (poly)aminoalkyl, and $C_2$–$C_6$ aminohydroxyalkyl radicals;
$R_5$ is chosen from linear and branched $C_1$–$C_6$ alkyl radicals optionally substituted with at least one radical chosen from $C_1$–$C_2$ alkoxy, hydroxyl, carboxyl, sulphonic (—$SO_3H$), and $NR_9R_{10}$ radicals; acylaminoethyl radicals; and 2-(2-hydroxyethyloxy)ethyl radicals; and $R_6$ is chosen from linear and branched $C_1$–$C_4$ alkyl radicals substituted with at least one radical chosen from hydroxyl, $C_1$–$C_2$ alkoxy, amino, $C_1$–$C_2$ (di)alkylamino, carboxyl, acylamino, (di)hydroxyalkylamino radicals; and 2-(2-hydroxyethyloxy)ethyl radicals;
wherein $R_9$ and $R_{10}$, which are independent of each other, are chosen from hydrogen atoms and $C_1$–$C_4$ alkyl radicals optionally substituted with at least one radical chosen from hydroxyl, amino, monoalkylamino, dialkylamino, alkoxy, and acylamino radicals.

19. The process according to claim 18, wherein the oxidizing agent is chosen from hydrogen peroxide, urea peroxide, alkali metal bromates, persalts, peracids, and oxidase enzymes.

20. The process according to claims 18, wherein the oxidizing agent is mixed at the time of application with the dye composition.

21. The process according to claim 18, wherein the oxidizing agent is applied to the fibers simultaneously with or sequentially to the dye composition.

22. A multi-compartment kit comprising a first dye compartment comprising a dye composition comprising, in a medium that is suitable for dyeing:
at least one oxidation base, and
at least one 6-alkoxy-2,3-diaminopyridine coupler of formula (I), or at least one addition salt thereof:

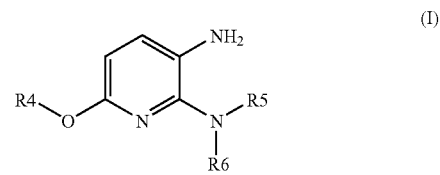

wherein:
$R_4$ is chosen from linear and branched $C_1$–$C_4$ alkyl radicals optionally substituted with at least one radical chosen from hydroxyl, $C_1$–$C_2$ alkoxy, and $NR_7R_8$ radicals wherein $R_7$ and $R_8$ are chosen from hydrogen atoms, $C_1$–$C_4$ alkyl, $C_2$–$C_6$ (poly)hydroxyalkyl, $C_2$–$C_6$ (poly)aminoalkyl, and $C_2$–$C_6$ aminohydroxyalkyl radicals;
$R_5$ is chosen from linear and branched $C_1$–$C_6$ alkyl radicals optionally substituted with at least one radical chosen from $C_1$–$C_2$ alkoxy, hydroxyl, carboxyl, sulphonic (—$SO_3H$), and $NR_9R_{10}$ radicals; acylaminoethyl radicals; and 2-(2-hydroxyethyloxy)ethyl radicals; and
$R_6$ is chosen from linear and branched $C_1$–$C_4$ alkyl radicals substituted with at least one radical chosen from hydroxyl, $C_1$–$C_2$ alkoxy, amino, $C_1$–$C_2$ (di)alkylamino, carboxyl, acylamino, (di)hydroxyalkylamino radicals; and 2-(2-hydroxyethyloxy)ethyl radicals;
wherein $R_9$ and $R_{10}$, which are independent of each other, are chosen from hydrogen atoms and $C_1$–$C_4$ alkyl radicals optionally substituted with at least one radical chosen from hydroxyl, amino, monoalkylamino, dialkylamino, alkoxy, and acylamino radicals; and
at least one second compartment comprising an oxidizing composition.

23. A 6-Alkoxy-2,3-diaminopyridine compound of formula (I) or an addition salt thereof:

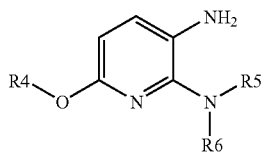 (I)

wherein:

$R_4$ is chosen from linear and branched $C_1$–$C_4$ alkyl radicals optionally substituted with at least one radical chosen from hydroxyl, $C_1$–$C_2$ alkoxy, and $NR_7R_8$ radicals wherein $R_7$ and $R_8$ are chosen from hydrogen atoms, $C_1$–$C_4$ alkyl, $C_2$–$C_6$ (poly)hydroxyalkyl, $C_2$–$C_6$ (poly)aminoalkyl, and $C_2$–$C_6$ aminohydroxyalkyl radicals;

$R_5$ is chosen from linear and branched $C_1$–$C_6$ alkyl radicals optionally substituted with at least one radical chosen from $C_1$–$C_2$ alkoxy, hydroxyl, carboxyl, sulphonic (—$SO_3H$), and $NR_9R_{10}$ radicals; acylaminoethyl radicals; and 2-(2-hydroxyethyloxy)ethyl radicals; and $R_6$ is chosen from linear and branched $C_1$–$C_4$ alkyl radicals substituted with at least one radical chosen from hydroxyl, $C_1$–$C_2$ alkoxy, amino, $C_1$–$C_2$ (di)alkylamino, carboxyl, acylamino, (di)hydroxyalkylamino radicals; and 2-(2-hydroxyethyloxy)ethyl radicals;

wherein $R_9$ and $R_{10}$, which are independent of each other, are chosen from hydrogen atoms and $C_1$–$C_4$ alkyl radicals optionally substituted with at least one radical chosen from hydroxyl, amino, monoalkylamino, dialkylamino, alkoxy, and acylamino radicals, wherein said compound of formula (I) Is not 2-(N-methyl-N-(β-hydroxyethyl)amino)-3-amino-6-methoxypyridine.

\* \* \* \* \*

UNITED STATES PATENT AND TRADEMARK OFFICE
CERTIFICATE OF CORRECTION

PATENT NO.         : 7,238,211 B2                                    Page 1 of 1
APPLICATION NO. : 10/678649
DATED                 : July 3, 2007
INVENTOR(S)       : Laurent Vidal et al.

It is certified that error appears in the above-identified patent and that said Letters Patent is hereby corrected as shown below:

Column 61, line 16, after "naphthalene-based couplers", insert a comma.

Column 62, line 16, "claims 18," should read --claim 18,--.

Column 62, line 66, "A 6-Alkoxy-2,3-diaminopyridine" should read --A 6-alkoxy-2,3-diaminopyridine--.

Column 64, line 15, "formula (I) Is not" should read --formula (I) is not--.

Signed and Sealed this

Second Day of October, 2007

JON W. DUDAS
*Director of the United States Patent and Trademark Office*